United States Patent [19]
Reed

[11] Patent Number: 6,052,184
[45] Date of Patent: Apr. 18, 2000

[54] MINIATURE, SUBMERSIBLE, VERSATILE, LIGHT SCATTERING PROBE FOR ABSOLUTE EQUILIBRIUM AND NON-EQUILIBRIUM CHARACTERIZATION OF MACROMOLECULAR AND COLLOIDAL SOLUTIONS

[75] Inventor: Wayne F. Reed, New Orleans, La.

[73] Assignee: The Administrators Of The Tulane Educational Fund, New Orleans, La.

[21] Appl. No.: 08/969,386

[22] Filed: Nov. 13, 1997

Related U.S. Application Data
[60] Provisional application No. 60/031,095, Nov. 13, 1996.

[51] Int. Cl.[7] .................................................. G01N 21/00
[52] U.S. Cl. .......................... 356/338; 356/337; 356/342; 356/441; 356/432
[58] Field of Search ..................................... 356/432, 433, 356/434, 435, 448, 440, 441, 410, 436, 338; 385/12, 13; 436/8; 422/82.06, 82.11

[56] References Cited

U.S. PATENT DOCUMENTS

| | | | |
|---|---|---|---|
| 3,850,525 | 11/1974 | Kaye | 356/73 |
| 3,954,342 | 5/1976 | Boeke | 356/206 |
| 4,265,535 | 5/1981 | Pitt | 356/70 |
| 4,363,551 | 12/1982 | Achter et al. | 356/338 |
| 4,548,500 | 10/1985 | Wyatt et al. | 356/336 |
| 4,616,927 | 10/1986 | Phillips et al. | 356/338 |
| 4,999,514 | 3/1991 | Silveston | 356/343 |
| 5,129,723 | 7/1992 | Howie et al. | 356/336 |
| 5,155,549 | 10/1992 | Dhadwal | 356/336 |
| 5,235,179 | 8/1993 | Chang et al. | 250/227.21 |
| 5,305,073 | 4/1994 | Ford | 356/338 |
| 5,350,922 | 9/1994 | Bartz | 356/338 |
| 5,434,667 | 7/1995 | Hutchins et al. | 356/338 |
| 5,638,174 | 6/1997 | Henderson | 356/343 |

FOREIGN PATENT DOCUMENTS
2166234A  4/1986  United Kingdom.

*Primary Examiner*—Robert H. Kim
*Assistant Examiner*—Roy M. Punnoose
*Attorney, Agent, or Firm*—Garvey, Smith, Nehrbass & Doody, L.L.C.

[57] ABSTRACT

A submersible light scattering probe for the absolute characterization of polymer and colloid solutions includes a ring member made of a preferably dark, opaque material, having embedded therein a plurality of optical fibers which can be connected to optical detectors remote from the probe. The ends of the optical fibers are preferably in direct contact with the fluid being tested. Instead of submersing the probe in a fluid, fluid can be caused to flow through the probe, placed in the probe, or placed in a transparent vessel placed in the probe. Individual large scattering particles can also be detected, counted, and characterized at the same time absolutes characterization of the polymer or colloid solution is performed.

59 Claims, 10 Drawing Sheets

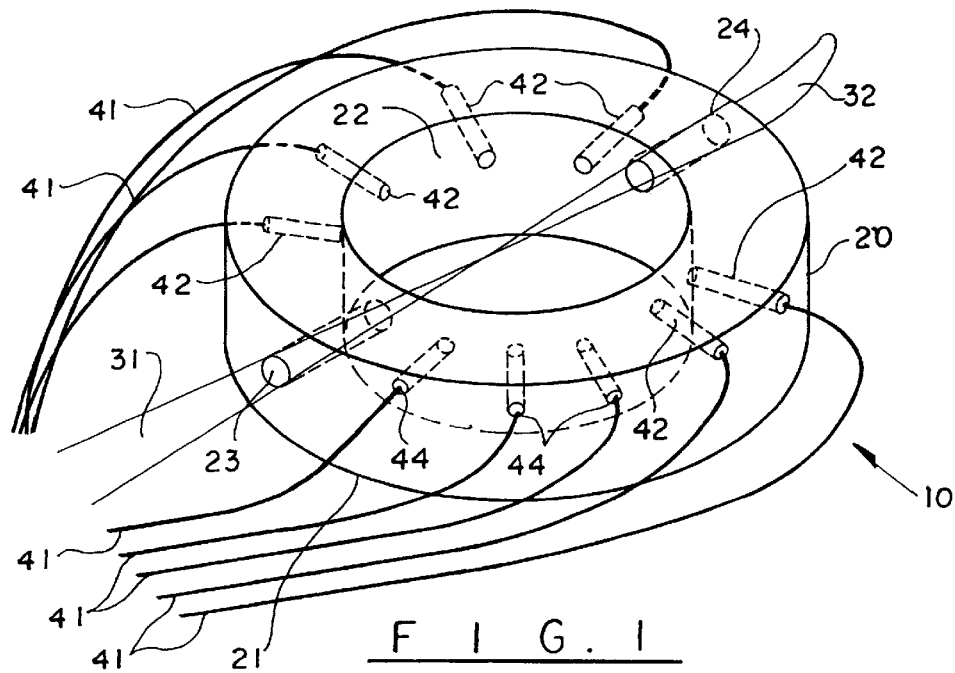
F I G. 1
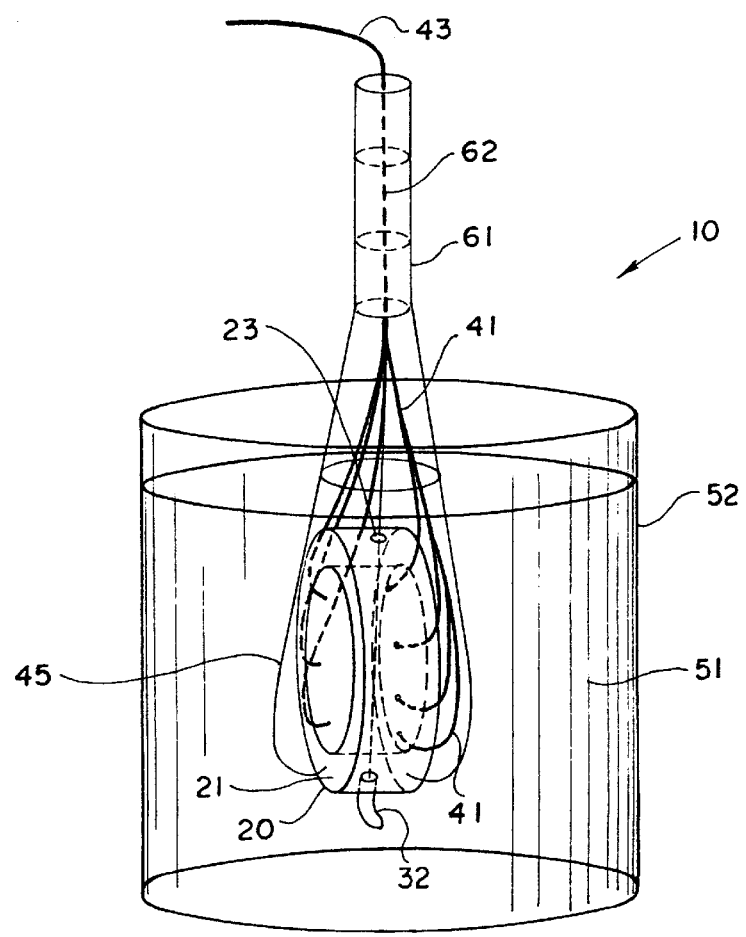
F I G. 2

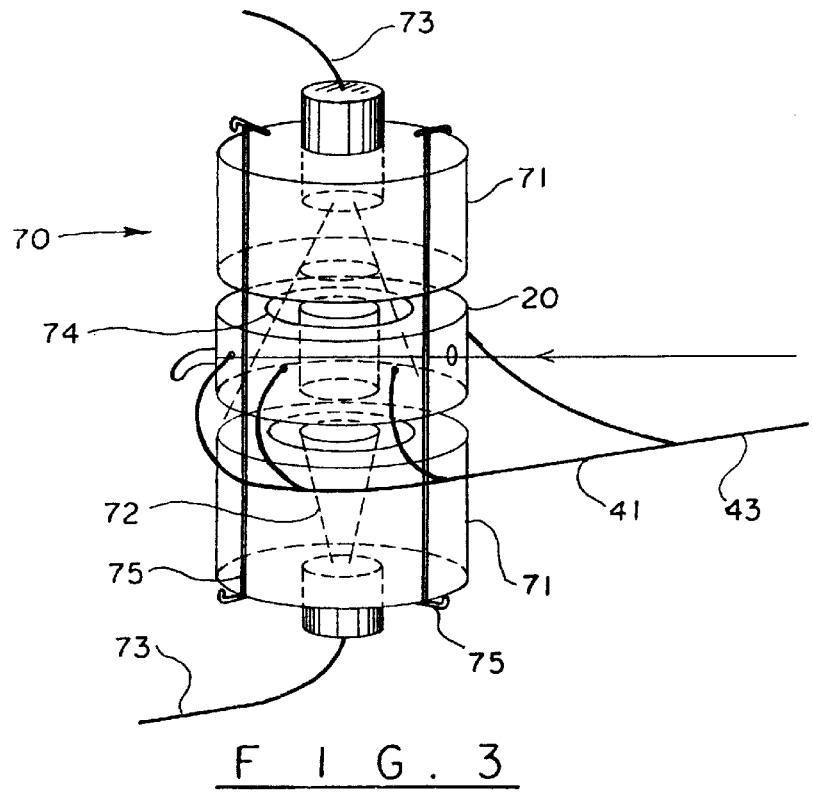
F I G. 3
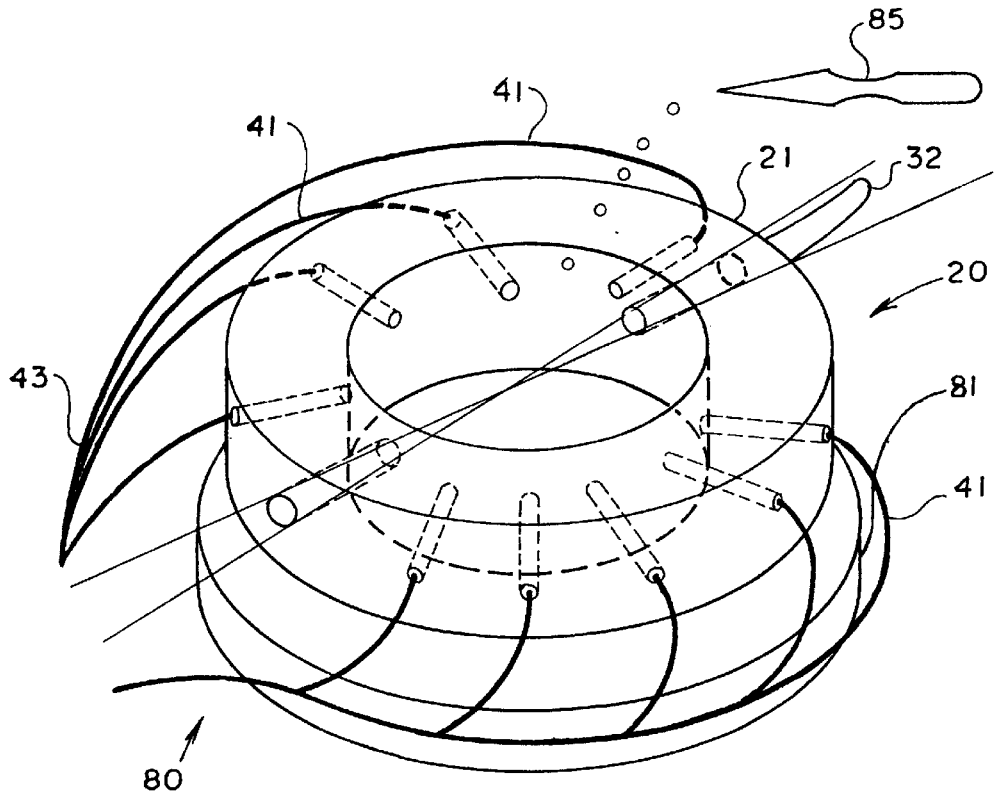
F I G. 4

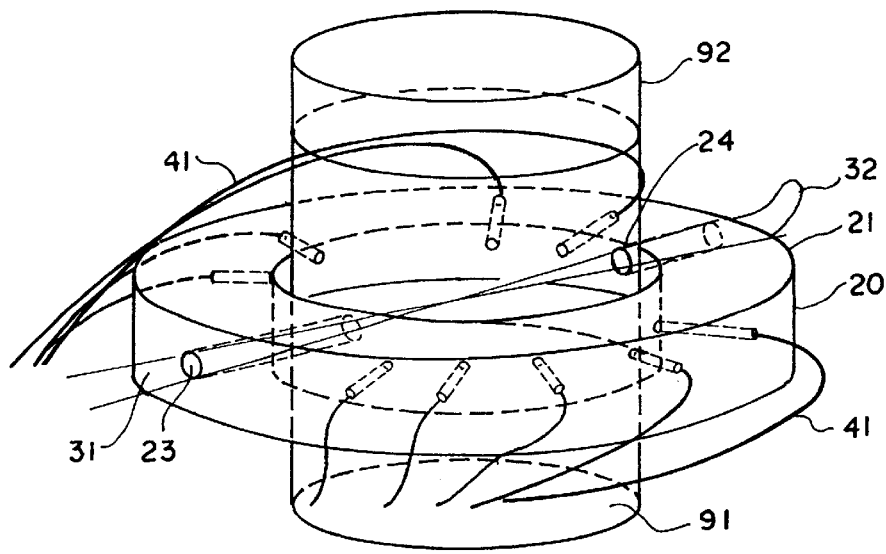
F I G. 5
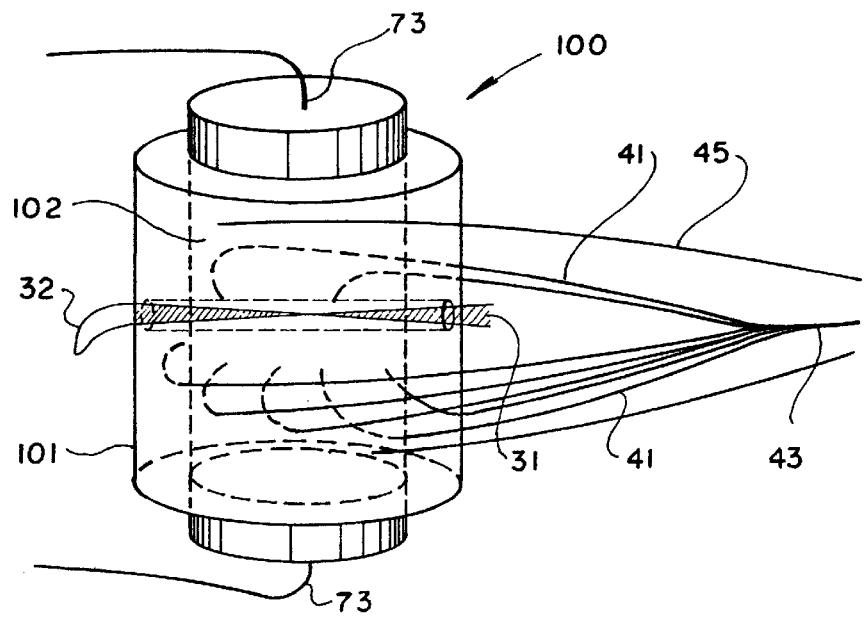
F I G. 6

MINIATURE, SUBMERSIBLE, VERSATILE, LIGHT SCATTERING PROBE FOR ABSOLUTE EQUILIBRIUM AND NON-EQUILIBRIUM CHARACTERIZATION OF MACROMOLECULAR AND COLLOIDAL SOLUTIONS

CROSS-REFERENCE TO RELATED APPLICATIONS

Priority of my U.S. Provisional Patent Application Ser. No. 60/031,095, filed Nov. 13, 1996, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to the absolute characterization of microscopic particles in solution. More particularly, the present invention relates to the absolute characterization of microscopic particles, such as polymers and colloids using static light scattering (SLS) and time-dependent static light scattering (TDSLS). In principle, the size range of detectability should run from about 20 Angstroms to 100 microns, with useful measurability in the range from 20 Angstroms to 2 microns, and a preferred range from about 20 Angstroms to 5000 Angstroms. Stated in terms of molar mass, the detectable range of particles should run from about 500 g/mole to $10^{14}$ g/mole, with useful measurability in the range of 500 g/mole to $10^9$ g/mole, with a preferred range from about 1000 g/mole to $10^7$ g/mole.

The preferred use of this invention is the determination of average, particle masses, static dimensions, interaction coefficients, and other properties, as well as their changes in time, when scattering is from a very large number of particles. This is to be distinguished from turbidometric and nephelometric techniques, in which turbidity or relative scattering of solutions is measured and compared to relative reference solutions, in order to obtain concentration of particles. The SLS technique employed refers to absolute macromolecular characterization, and not to determinations of concentrations of particulates with respect to specific relative calibration, etc. This is also to )e distinguished from devices which count and characterize single particles, although the present invention can count and characterize single particles, in addition to making SLS measurement. The least number of particles whose scattered light would be detected in the scattering volume (the volume of illuminated sample whose scattering is measured by a given photodetector) would be or the order of 20 and the maximum on the order of $4 \times 10^{17}$, with the preferred range being from about 15,000 to $1.5 \times 10^{13}$ particles. In terms of concentration of solute (dissolved polymer or colloid) the range would be from about $10^{-8}$ g/cm$^3$ (for very large particles) to 0.2 g/cm$^3$ (for very small particles) with the preferred range being from about $10^{-6}$ to $10^{-1}$ g/cm$^3$. It should be pointed out that SLS in the absolute mode requires optically transparent solutions in which single, not multiple, scattering, dominates. Many particle concentration detectors actually work in turbid, solutions, which is a different range of conditions entirely.

SLS has proven to be a useful technique not only for characterizing equilibrium properties of microscopic particles, such as molar mass, dimensions and interactions, but also for following) time-dependent processes such as polymerization, degradation and aggregation. Measuring the time-independent angular distribution and absolute intensity of scattered light in the equilibrium cases allows the former properties to be determined, according to procedures set forth by Lord Rayleigh, Debye, Zimm and others (e.g. ref. 1). In particular, this invention can be used is conjunction with the well known procedure of Zimm to determine weight average molar mass $M_w$, z-average mean square radius of gyration $<S^2>_z$ and second virial coefficient $A_2$. Measuring the time-dependent changes in the scattered intensity allows calculation of kinetic rate constants, as well as deduction of kinetic mechanisms and particle structural features (e.g. ref. 2,3). TDSLS can be used to monitor polymerization and degradation reactions, aggregation, gelling and phase separation phenomena (e.g. ref 4).

In addition to absolute SLS and TDSLS measurements, the present invention can also simultaneously count and characterize individual particles which are much larger than the principal polymer or colloid particles; e.g., the large particles may have a radius of 5 microns, whereas the polymer may have an effective radius of 0.1 micron. The large particles may represent a contaminant or impurity, or may be an integral part of the solution, e.g., bacteria (large particles) produce a desired polymer (e.g., a polysaccharide) in a biotechnology reactor. The number density of bacteria can be followed in time, and the absolute macromolecular characterization of the polysaccharide could also be made (an auxiliary concentration detector would also be necessary if the polysaccharide concentration changes in time).

2. General Background of the Invention

SLS is currently used for three main purposes in academic, medical and industrial research and development, and industrial quality control; 1) to characterize useful averages of mass, mean square radius of gyration and second virial coefficient for unfractionated particles in equilibrium, using traditional procedures, 2) to characterize heterogeneous populations of particles which have been fractionated by techniques such as size exclusion chromatography and 3) to follow time-dependent processes. As examples of each purpose: 1) A new biological macromolecule or microstructure is isolated, or a new polymer is synthesized, and its average macromolecular characteristics are determined by SLS. A manufacturer of synthetic polymers, for water treatment, paints, coatings, adhesives, etc., would use SLS for quality control of their product. 2) A synthetic or biological polymer sample contains a wide variety of molar masses (polydispersity), and it is desirable to determine the mass and dimension distribution using a fractionation technique coupled to SLS. The purpose of this can be for fundamental research into a biological mechanism, to aid development of new products, to establish quality control specifications of new products, or tc assess the effects of different chemical or physical treatments on the product, etc. 3) It is desired to determine how quickly a polymer degrades under attack by such agents as enzymes, heat, radiation, ultrasound, etc., and this can be determined by TDSLS. This will guide studies in developing new pharmacological inhibitors or promoters, or resistant plastics, or biodegradable materials. A central problem of great economic interest, in which TDSLS can be used is to have an on-line method for determination of the build up of molecular weight during industrial polymerization processes. A further use of the present invention will be in the simultaneous measurement of SLS and particle counting in heterogenous solutions.

Clearly, SLS and TDSLS have a wide range of applications, including, but by no means limited to products such as pharmaceuticals, foodstuffs, resins, plastics, coatings, inks, adhesives, liposomes, cosmetics, water treatment and paper making chemicals, paints, additives, plasticizers, microencapsulation structures, etc.

Current technology generally consists of a transparent, hollow sample cell, usually of glass or quartz, into which a scattering sample is introduced and through which a light beam (usually from a laser) is passed. The scattered light then passes through the walls of the transparent cell, where photodetectors or fiber optic pick-ups are placed. The signal from the detected scattered light is then processed and the properties of the scattering sample deduced. Such systems require that sample be introduced into the cell, remote from the main sample batch itself. A disadvantage of a transparent sample cell is that it creates interfaces between incident light and the sample which produce unwanted stray light or 'glare'. This stray light or glare, constitutes one of the major pitfalls and nuisances in the actual practice of SLS. Such cells are also relatively expensive and require fairly precise alignment for proper performance.

The present invention includes a (preferably miniaturized) submersible probe which can be brought into the sample, rather than vice versa. No transparent cell need intervene between the sample solution, the incident beam and the optical detectors. This reduces the SLS instrument to a small probe, which can be thought of now as a simple lab probe, like that of a pH or conductivity meter, to be used simply and routinely. The probe portion is relatively inexpensive to fabricate, easy to align, and can even be made to be disposable. The photodetectors, signal processing, etc. are normally remote from the probe. It is anticipated that such an SLS/TDSLS probe is substantially more economical, versatile and easy to use than currently available systems. The present invention can be used in a variety of modes for both time-independent and time-dependent measurements; 1) Submersible mode, in which the probe is submerged in a vessel containing sample solution, such as a beaker, test tube, vat, reactor, etc. 2) Fill mode, in which small amounts of sample liquid (about 3 microliters to 30 milliliters, for example) can be simply pipetted, scooped, or otherwise transferred into the probe body. 3) Flow mode, in which by means of an integrally flanged pump, or hydraulic connection to a tube with flowing sample, the sample liquid flows through the invention. This can be used for unfractionated samples, including those undergoing time-dependent processes (polymerization, degradation, cross-linking, etc.), or samples solutions fractionated by SEC or other means. 4) Insert mode in which a standard glass vial or cell containing sample liquid is inserted into the probe body, instead of filling the probe body, immersing it, or flowing the sample through it. This would be used instead of any of the other three modes, when, for example, the sample may be deleterious for the chamber, because of causticity, gelling, precipitation, etc. It can also be convenient and valuable when many samples are independently prepared and are to be measured separately, and/or when the state of prepared samples in sealed cells is to be checked periodically, without disturbing the sample due to flow, pipetting, etc. The demands of a wide variety of users can be satisfied by simply changing low cost, optical probe assembly, since the detection, electronics, computer interfacing and basic software are the same.

Brief Comparison with other Light Scattering Devices

The present invention is distinct from other light scattering devices. For example: U.S. Pat. No. 4,616,927 (Phillips, Reece and Wyatt) and U.S. Pat. No. 5,305,073 (Ford) describe the use of highly polished, optically transparent cell for absolute light scattering measurements. The current invention requires no optically transparent cell. Neither of these inventions are submersible, nor can either be considered as a 'probe' which can go into the sample liquid being measured. Neither, hence, can fulfill the probe function of the current invention, and both are also less versatile, and more costly in general. A submersible light scattering probe is presented by U.S. Pat. No. 5,350,922 (Bartz), but is designed for relative measurements of fairly turbid media (e.g., muds in suspension in water). They collect scattered light, indiscriminately, from 0 to 180° scattering angles, and hence cannot perform absolute light scattering on samples requiring exact specification of the scattering angle (their system could work for Rayleigh scatterers, i.e. for sizes much smaller than the incident radiation wavelength; since they are chiefly looking at particulates in suspension, which are generally very large, this condition would not be expected to be met). Furthermore, their device does interpose an optically transparent medium between the light source and the sample liquid and the detector and the sample liquid. In addition, that device cannot be used in either 'fill mode' nor flow mode, and hence is also considerably less versatile. None of these inventions mentioned have the versatility and interchangeability of the present invention.

The use of simultaneous multi-angle detection is shown in U.S. Pat. No. 3,850,525, "Simultaneous Multiple Measurements in Laser Photometers".

The following patents documents are incorporated herein by reference:

U.S. Pat. Nos. 3,850,525; 3,954,342; 4,265,535; 4,363,551; 4,548,500; 4,616,927; 4,995,514; 5,129,723; 5,155,549; 5,235,179; 5,305,073; 5,350,922; 5,434,667; 5,638,174; and Great Britain Patent Application No. 2166234.

BRIEF SUMMARY OF THE INVENTION

The present invention is the first fully submersible SLS probe for absolute macromolecular characterization (as opposed to particle counting, nephelometry, dynamic light scattering, or relative concentration measurements). The optical assembly of the present invention can be completely immersed in the scattering medium. Thus, the present invention includes a scattering probe which can 'go into' the medium to be measured (e.g. into test tubes, production vats, etc.), and samples of the scattering medium need not be introduced into a transparent sample cell remote from the medium itself, as is done in current systems. In the present invention the probe can be submerged in a variety of harsh environments, as concerns temperature, pressure and solvents, and communicates to the remote electronic and signal processing portion via a harness containing fiber optic cables.

The present invention can be used in several distinct modes (immersion, fill mode, insert mode and flow mode), giving it wide versatility. The probe of the present invention is rot constrained to be immersed in order to function. A small quantity of sample can also be placed in the optical assembly compartment for measurement in a 'fill mode'. A sample in a transparent vial or cell can also be placed in the chamber or ring member for measurement. Also, the probe can be hooked into a flowing stream of sample liquid for use in different applications such as polymer separation (e.g. size exclusion chromatography), and on-line, unfractionated flows of polymers in a vessel in equilibrium, or undergoing polymerization, aggregation, cross-linking or degradation processes.

The present invention can respond to the needs of a wide variety of users and applications by simply changing the inexpensive optical assembly, since the detection, electronics, computer interfacing and basic software are all the same. For example, a miniature probe with a 10 microliter channel could plug into the same 'detection/analysis' back-end as a 50 milliliter optical probe designed for immersion at high temperatures. There is wide room for substitution of different diameter fibers with different acceptance angles, number of photodetectors on the 'detection/analysis' back-end, etc.

The present invention does not require a transparent sample cell for the scattering solution. Unlike all current SLS systems for absolute macromolecular and colloidal characterization, no glass or other transparent cell need intervene between the sample, the detection fibers and the fiber or lens used for introducing the incident beam. Major advantages which this confers includes avoiding the expense, maintenance and cleaning of transparent cells, and minimizing glare and stray light, because the optical assembly is preferably made from a very dark or black material, and hence does not have highly reflective glass and/or other dielectric surfaces causing spurious glare and reflections.

The optical probe portion of the present invention is preferably miniature in scale. Whereas other devices also use only small sample volumes, those devices require that the sample be pumped or injected in through appropriate plumbing. In the present invention, when used in the fill mode, small quantities of sample can be simply pipetted or dropped into the optical assembly compartment, where they reside during the measurement.

The probe can achieve both absolute calibration and self-cleaning simultaneously when immersed in a proper solvent, such as toluene. Furthermore, because of the direct immersion there are no problems with index of refraction corrections associated with cells which do not maintain cylindrical symmetry about an axis perpendicular to the scattering plane. Hence, well-known, non-proprietary standard calibration procedures can be used for each detector.

The versatile scattering chamber is very inexpensive to fabricate and, in some instances, can be even treated as disposable. This contrasts to the generally high cost of the scattering cell/detector assembly in prior art units.

Unlike existing SLS units, the use of fiber optic detectors and narrow beam focusing make the system quite insensitive to alignment. This has the significant advantage of allowing the unit to operate with a simple coarse alignment, whereas a high degree of alignment is normally required in existing systems. This is achieved because the acceptance cone of the fibers is fairly large (typically 9°) and the beam is collimated to usually less than 100 microns. Hence, at a remove of 3 mm from the fiber, the beam can be moved up and down approximately 0.5 mm for a 9° acceptance angle fiber, without significantly changing the amount of scattered light entering the fiber.

Properly minimizing the scattering volume with a focused beam and using fiber optic detectors and fast detection electronics allow unfiltered samples to be measured, even when no flow or other relative motion between sample and detector exists. This is a major advance, considering that SLS in conventional instruments only became reliable after chemical filtration technologies improved considerably.

The present invention includes a submersible device, which measures relative light scattered at various angles from a large number of scattering particles, from which absolute macromolecular and colloidal characterization is made, via well known, non-proprietary calibration procedures and the well known procedures of Zimm and others. The device need not contain an optically transparent cell interposed between the scattering medium and the incident optic delivering the incident beam and the optical fibers used for detection.

The submersible absolute macromolecular characterization device described in the previous paragraph preferably consists of a completely solid or perforated, or striated or otherwise partially open solid piece, a ring member or a cylinder with a channel inside into which sample liquid enters upon immersion. In this device, polarized or unpolarized incident light (provided by a laser or any other source of visible or ultraviolet light) is led into the channel and spatially filtered with any suitable optical elements such as a tubular lens, miniature convex lens, flat window, fiber optic, irises, etc., or any suitable combination. The light so led in can undergo any necessary degree of collimation, including none, in order to make as narrow an incident beam waist in the detected scattering volume as desired. Scattered light detection is preferably achieved by fiber optic strands, or other fiber optic light conduits, which are exposed to scattered light in the channel, either by virtue of being recessed into the walls of the channel, being flush with the walls of the channel, or protruding into the channel. The degree of collimation of incident light and the diameter of the detecting fibers are combined to optimize the detected scattering volume for the particular sample to be measured. The transmitted incident light is preferably 'dumped' using any standard beam dump arrangement, such as a hole, Rayleigh horn, prism, etc. The channel is preferably black or blackened to reduce glare and stray light from the incident beam. The delivery and detection optical train elements are preferably gathered into a harness leading to the photodetectors, amplifiers and computer external to the light scattering probe.

Instead of the probe mentioned above which can be immersed in sampling liquid, a different probe can be provided, into whose channel, plugged at one end, rather, a small quantity of sample liquid can be transferred (e.g. by pipette, or by scooping) and therein reside while the scattering measurements are made.

Likewise, a third probe having suitable liquid flow connectors need not be immersed in sampling liquid; instead, through its channel the sample liquid can be made to flow for scattering measurements.

The submersible absolute macromolecular characterization device described above can consist of a ring member, not necessarily closed or circular (e.g. rectangular, elliptical, horseshoe, or any other shape capable of holding the light source fixed relative to the, detection fibers (or photodetector when detection fibers are not used)) containing the incident beam delivery optics, beam dump and detection fibers, and which can be immersed directly in a sample liquid for scattering measurements. Alternatively, the submersible absolute macromolecular characterization device described above can consist of a ring member, not necessarily closed or circular (e.g. rectangular, elliptical, horseshoe, etc.) which can be placed inside of a chamber in a cell of appropriate dimension, so as to protect it from the liquid it is immersed in, ambient light or other factors, or to otherwise control how sample liquid reaches the ring member for scattering measurements.

The present invention includes a method whereby any of the devices described above, with appropriately small scattering volume, can be used to measure sample solutions which may contain significant numbers of large scattering contaminants by using fast enough photodetector response to identify, count and eliminate scattering intensity spikes produced by the contaminants, thereby enabling the recovery of the uniform scattering background due to the population of polymers or colloids in the sample. The sample may be either stationary or flowing to accomplish this. Very roughly, the number density of contaminant particles can be on the order of one per scattering volume, so that very tiny scattering volumes allow for relatively higher concentrations of impurity to be present. The identified spikes can be counted and used to assess the particle density of large particles in a solution, and how this number may change in time, as well as simultaneously determining the absolute uniform scattering from a population of polymer or colloids.

The present invention also includes a method whereby the flow mode of the present invention described herein can be used to measure, in real-time, the increase of the weight average molecular weight of polymers being produced in a solution of chemicals undergoing polymerization reactions. This method preferably includes the on-line dilution of the polymer containing solution to bring it into a concentration range where useful, absolute scattering can be measured. This range is where the quantity $2A_2cM_w$, is preferably smaller than 1, but can actually be as much as 10. Such dilution can be achieved by the use of hydraulically pulling polymer solution and pure solvent through an hydraulic 'T' or other mixing chamber via a pump or other flow-causing device. A concentration sensitive detector is preferably installed in the line of fluid flow so as to determine in real-time the actual concentration of polymer in the diluted solution Such a detector may be a refractive index monitor, ultraviolet or visible spectrophotometer, etc.

The present invention also includes a method whereby any of the devices herein described are used to monitor the changes in time of polymer solutions which are undergoing, degradation, polymerization, aggregation, gelling, or phase separation.

The present invention also includes a method whereby any of the devices herein described are used to usefully characterize heterogeneous solutions, containing populations of both polymers or colloids and large particulate scatterers, whether either or both of these changes in time or not.

The present invention comprises a kit including light scattering devices of the type described herein, whereby a wide variety of optical probes (with widely varying dimensions, sample capacities, fiber optic types, numbers of angles) made of different materials to withstand different environments can be connected to the same 'back-end' of detection electronics, signal processing and data analysis. The kit can also include the detection electronics, signal processing and data analysis.

BRIEF DESCRIPTION OF THE SEVERAL VIEWS OF THE DRAWINGS

For a further understanding of the nature, objects, and advantages of the present invention, reference should be had to the following detailed description, read in conjunction with, the following drawings, wherein like reference numerals denote like elements and wherein:

FIG. 1 is a perspective view of the preferred embodiment of the apparatus of the present invention;

FIG. 2 is a side view of the preferred embodiment of the apparatus of the present invention immersed in a sample liquid;

FIG. 3 is a side view of the preferred embodiment of the apparatus of the present invention being used in a flow mode;

FIG. 4 is a perspective view of the preferred embodiment of the apparatus of the present invention being used in a fill mode;

FIG. 5 is a perspective view of the preferred embodiment of the apparatus of the present invention being used in an insert mode; and FIG. 6 is a perspective view of an alternative embodiment of the apparatus of the present invention;

DETAILED DESCRIPTION OF THE INVENTION

Figure 7:
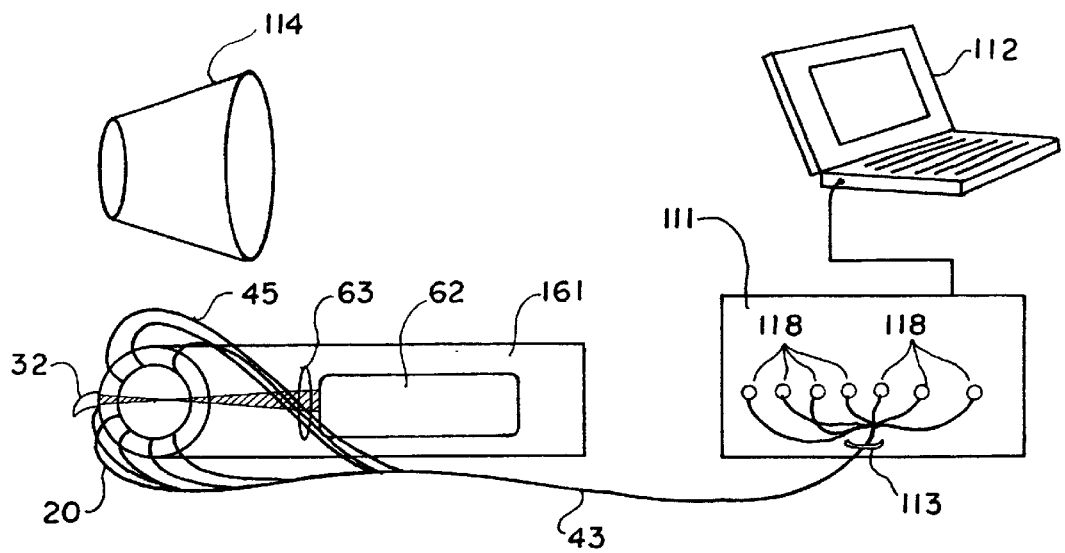
FIG. 7 is a schematic of how a diode laser might be incorporated into a base plate in a ring member version of the present invention.

The preferred embodiment of the present invention is a submersible light probe 20 (see FIG. 1) including a ring member 21 made of a preferably dark, opaque material, having embedded therein a plurality of optical fibers 41 which can be connected to optical detectors 118 (see FIG. 7) remote from the probe 20. The ends 44 of the optical fibers 41 are preferably in direct contact with the fluid 51 (see FIG. 2) being tested. In a first variation of the invention (see FIG. 3), fluid is caused to flow through the probe 20. In a second variation (see FIG. 4), a base plate 81 is added so that the ring member 21 can contain a fluid to be tested. In a third variation of testing (see FIG. 5), a clear container containing fluid to be tested is placed through the ring member 21. In yet another variation of the invention (preferably only when the probe is not submersible), photodetectors can replace the optical fibers.

The purpose of the probe is to measure light scattering by particles in a fluid (static light scattering (SLS)).

It is believed that this is the first probe for SLS or TDSLS where light detectors (the optical fibers) are actually in the fluid, as opposed to being separated from the fluid by glass or some other media.

FIG. 1 is a perspective view of the minimal ring member version 20 of the present invention. FIG. 1 shows the essential layout of the ring member-version optical assembly 20, with fiber optic detectors 41, beam dump 32, and a laser beam 31 entering a chamber 22 through a window 23, either through local mounting and lensing, or via fiber optic transfer through one of the harness fibers. The ring member channel 22 may alternatively have a square or polygonal cross-section, instead of circular, which may be particularly useful for single or few angle detection. Such single or few angle detection may warrant simply mounting photodiodes on the side of the chamber, rather than using fiber optics. The ring member o.d. and i.d can vary widely, depending on the application (specific dimensions for test versions are given in the "Experimental Verifications of the Invention", below). The range of i.d. can be, for example, from about 2 mm to 50 cm, with the o.d. being determined by desired wall thickness, which can, for example, range from about 1 mm to 10 cm. The length of the ring member can also, for example, vary from about 3 mm to 10 cm. Optionally a cowl 114 (see FIG. 7) made of rigid or flexible dark material can be placed over the ring member in any of its modes of operation to shield against ambient light.

FIG. 2 shows the immersion mode of the present invention. The ring member assembly 20 is attached to a handle 61. The hollow handle 61 contains an optical harness 43, which has been formed by drawing all the optical fibers 41 together. A sheath 45 on the outside of the ring assembly 20 protects the fibers 41 that are led into the harness 43. A diode laser 62 can be mounted directly on or to the handle 61 for an integral optical assembly/light source version, or the beam can be led in through a fiber optic in the harness 43.

FIG. 3 shows the flow mode of the present invention. Ring member assembly 20 is sandwiched between two end-pieces 71, each of which has a hydrodynamically shaped flow channel 72, and standard HPLC tubing and fittings 73 for liquid to be injected through the ring member assembly 20 via syringe, pump, etc. There are preferably O-rings 74 between the ring member 20 and the end-pieces 71, and the three pieces are held together by through-bolts 75, or a bracket.

FIG. 4 shows the fill mode of the present invention. Ring member assembly 20 can have a base plate 81 attached, so that sample solutions can be pipetted, scooped, or otherwise introduced into the channel, as with dropper 85. A simple modification of ring member assembly 20 could involve not boring the channel 22 all the way through the ring member assembly 20 instead of using a removable base plate 81.

FIG. 5 shows the insert mode of the present invention. A cylindrical vial or cell 92 containing sample solution 91 is simply inserted into ring member assembly 20. This can be advantageous where the sample 91 may be damaging to the ring member assembly 20, or where multiple samples are prepared and stored in vials and are to be measured individually on multiple occasions.

FIG. 6 shows the integral chamber version 100 of the probe of the present invention. By lengthening the ring member version, a one piece unit 100 can serve for both the flow chamber, to which HPLC connections are directly made, and for fill and immersion modes. Chamber o.d. and i.d. follow the ranges mentioned above, whereas the length for any given chamber can considerably exceed the ring member lengths; e.g., lengths can be from about 1 cm to 30 cm. Channel bore 102 can optionally be tapered. In FIG. 6, the laser input 31 can either be through lensing or via fiber.

FIG. 7 is a schematic of how a diode laser 62 might be incorporated on or into a base plate 161 in the ring member version 20 (applicable also to the chamber version 100). Also shown is an optional cowl or hood 114 to cover the ring member assembly 20 to reduce any effects of ambient light. Also shown is the overall schematic of the optical assembly attached via optical harness 43 to the photodiode/electronic assembly 111, which then transmits scattering signals to a microcomputer 112. If a remote laser is used, instead of on the base plate 161, then the laser would normally be housed with the photodetectors 118, and the beam led into the ring member assembly 20 or chamber 100 via a fiber in the optical harness 43. In FIG. 7, a converging lens 63 is used to focus the laser beam.

Figures 8, 9:
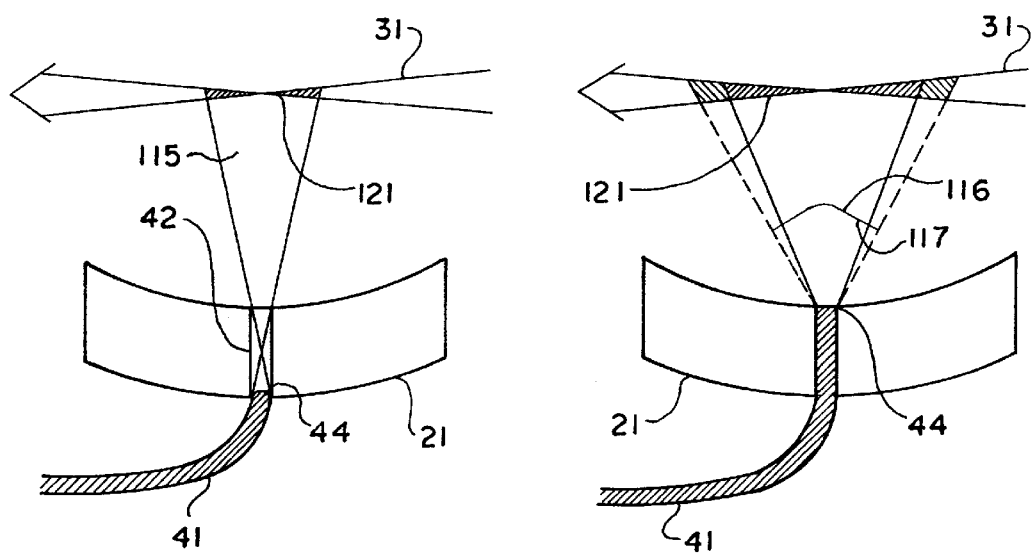
FIG. 8 is a schematic representation of a 'pinhole mode' of detection.
FIG. 9 is a schematic representation of an 'acceptance angle mode' of detection.

FIGS. 8 and 9 are schematic representation of detection modes. The 'pinhole mode' (FIG. 8) occurs when the fiber 41 is not completely inserted into the through-hole 42 in the chamber wall, and the angle defined by the end 44 of the fiber 41 and the end of the hole is less than the acceptance angle of the fiber 41 in the particular solvent in which it is immersed. The "acceptance angle mode" (FIG. 9) is when said angle is larger than the acceptance angle of the fiber, which means the acceptance angle of the fiber itself will define the scattering volume 121.

Figure 10:
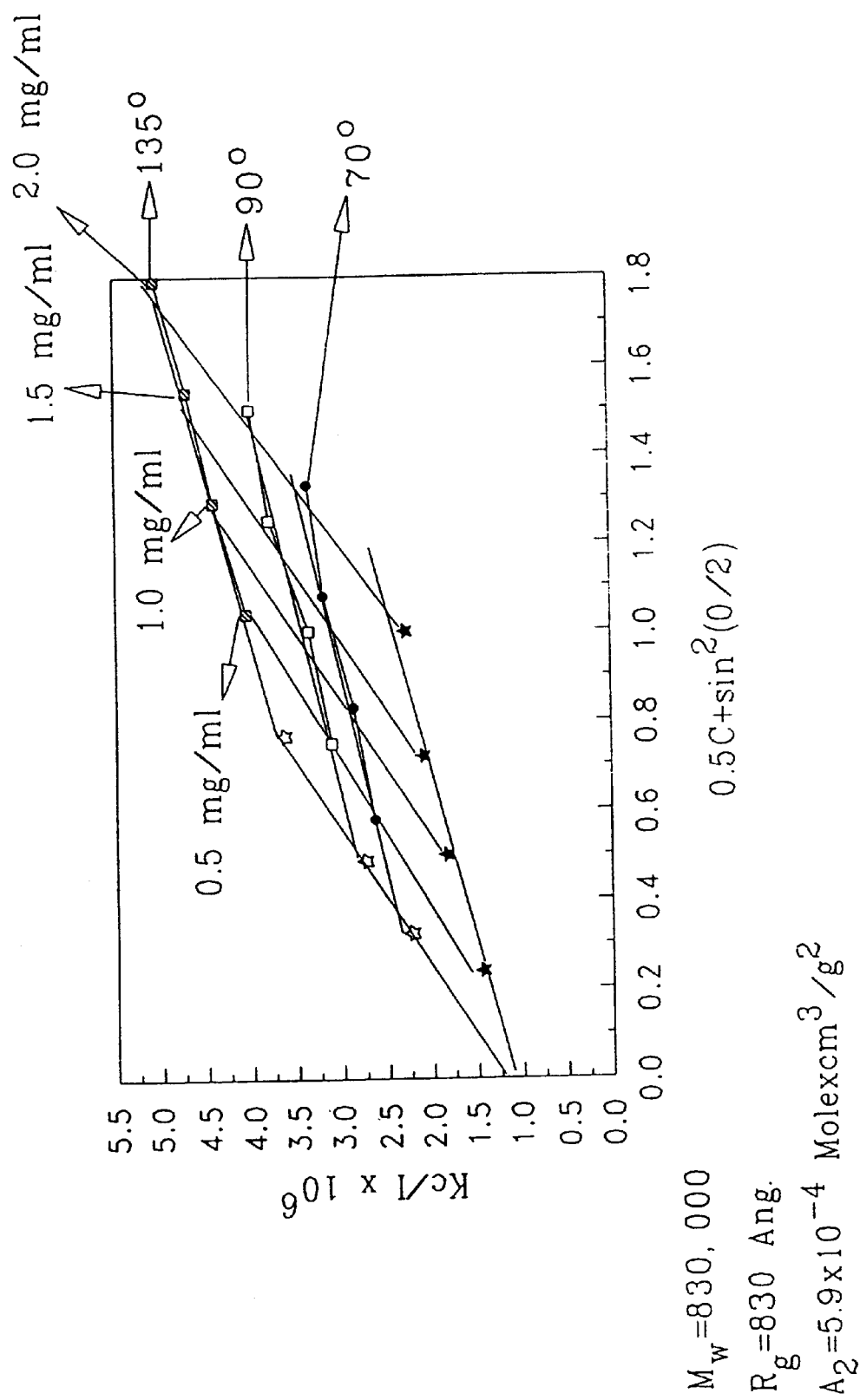
FIG. 10 shows fill mode Zimm plot for high molecular weight PVP irradiated with a 10 mW Argon ion laser and each angle calibrated to pure toluene.

FIG. 10 shows a fill mode Zimm plot for high molecular weight PVP.

Figure 11:
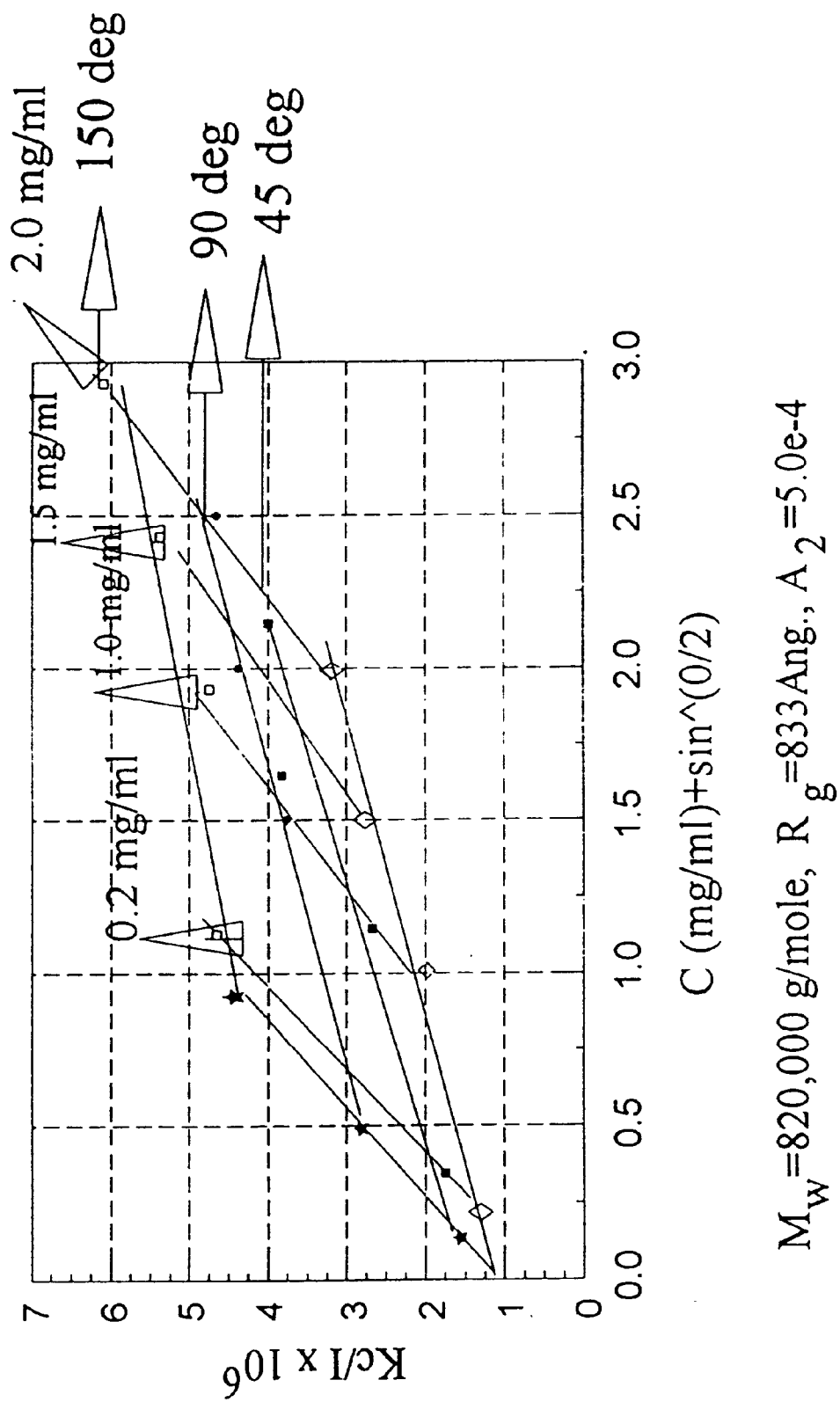
FIG. 11 shows an immersion mode Zimm plot for unfiltered solutions of high molecular weight PVP ("1.3MD" PVP) irradiated with a 10 mW Argon ion laser, using 150 micron optic fiber in 3 inch diameter vessels of solution.

FIG. 11 shows an immersion mode Zimm plot for high molecular weight PVP.

Figure 12:
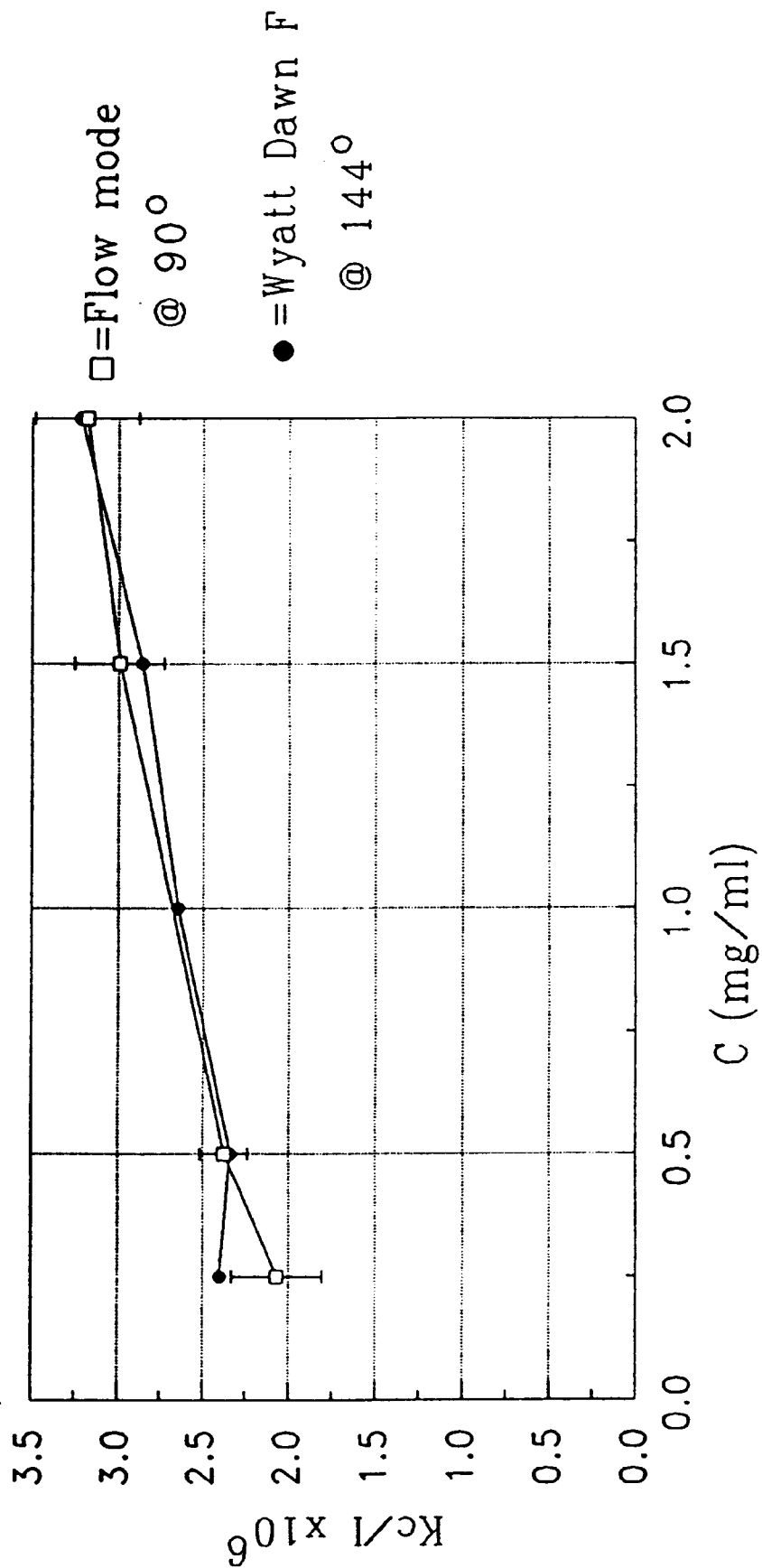
FIG. 12 shows a flow mode Debye plot for high molecular weight PVP at $\theta=90°$ irradiated with a 488 nm Argon ion laser, compared to the results of a Wyann Dawn-F at 144° (633 nm He—Ne laser), with error bars.

FIG. 12 shows a flow mode Debye plot for PVP at $\theta=90°$.

Figure 13:
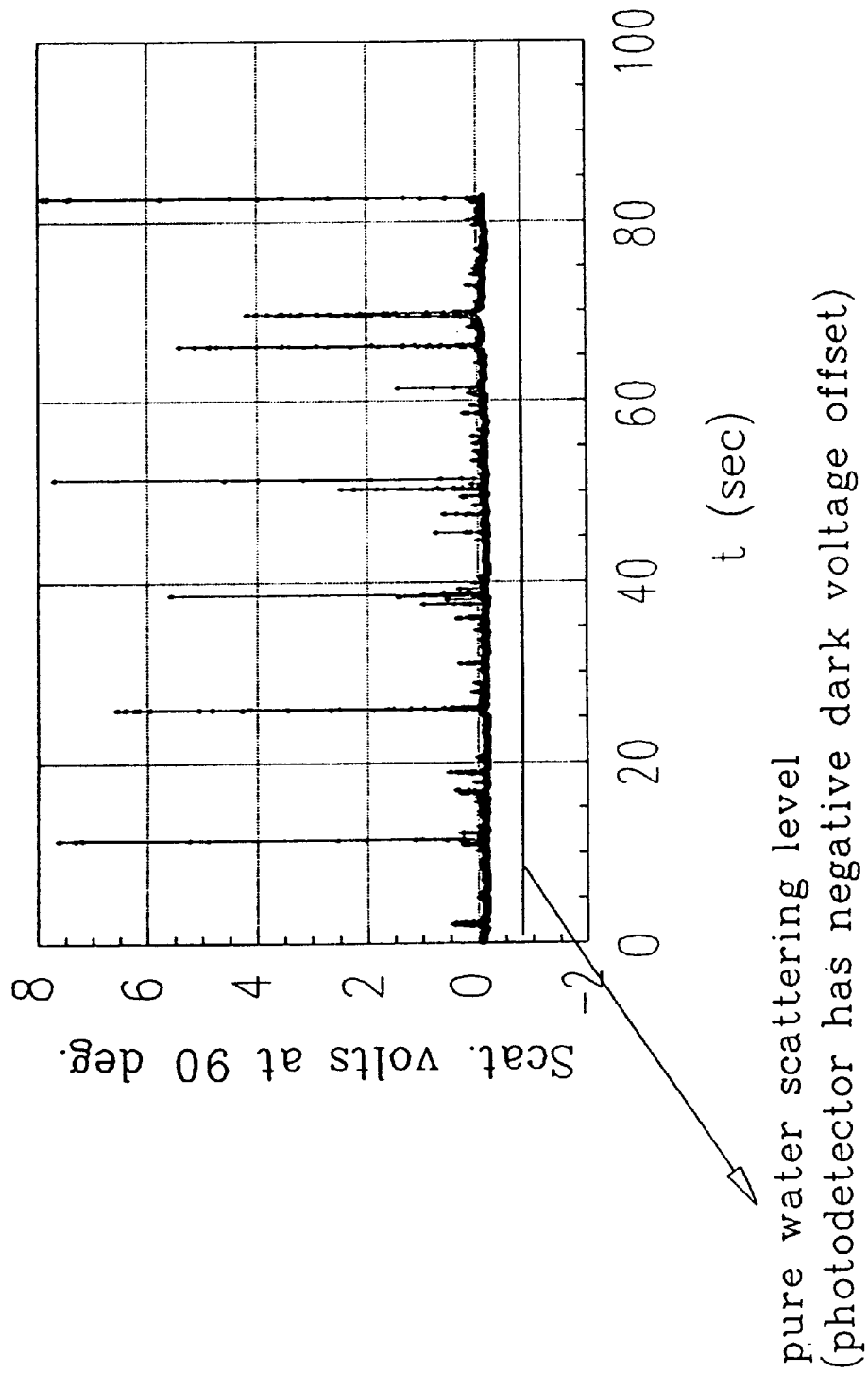
FIG. 13 shows a flow mode measurement of a 0.5 mg/ml high molecular weight PVP (1.3MD PVP) solution with "contamination" by 10 micron latex spheres, using a 300 micron optic fiber at 90° and 5 mW diode laser.

FIG. 13 shows a flow mode measurement of a 0.5 mg/ml high molecular weight PVP solution with 'contamination' by 10 micron latex spheres. The spheres were in a concentration of 40,000 particles/cc. It is possible both to count the number of spheres passing through the scattering volume, and obtain the absolute scattering due to the PVP, when using the program REEDFLO (see Appendix A) on DT2801a. Thus, the present invention can simultaneously conduct absolute macromolecular characterization of one substance and individual particle counting and characterizing techniques on another substance in the same fluid.

Figure 14:
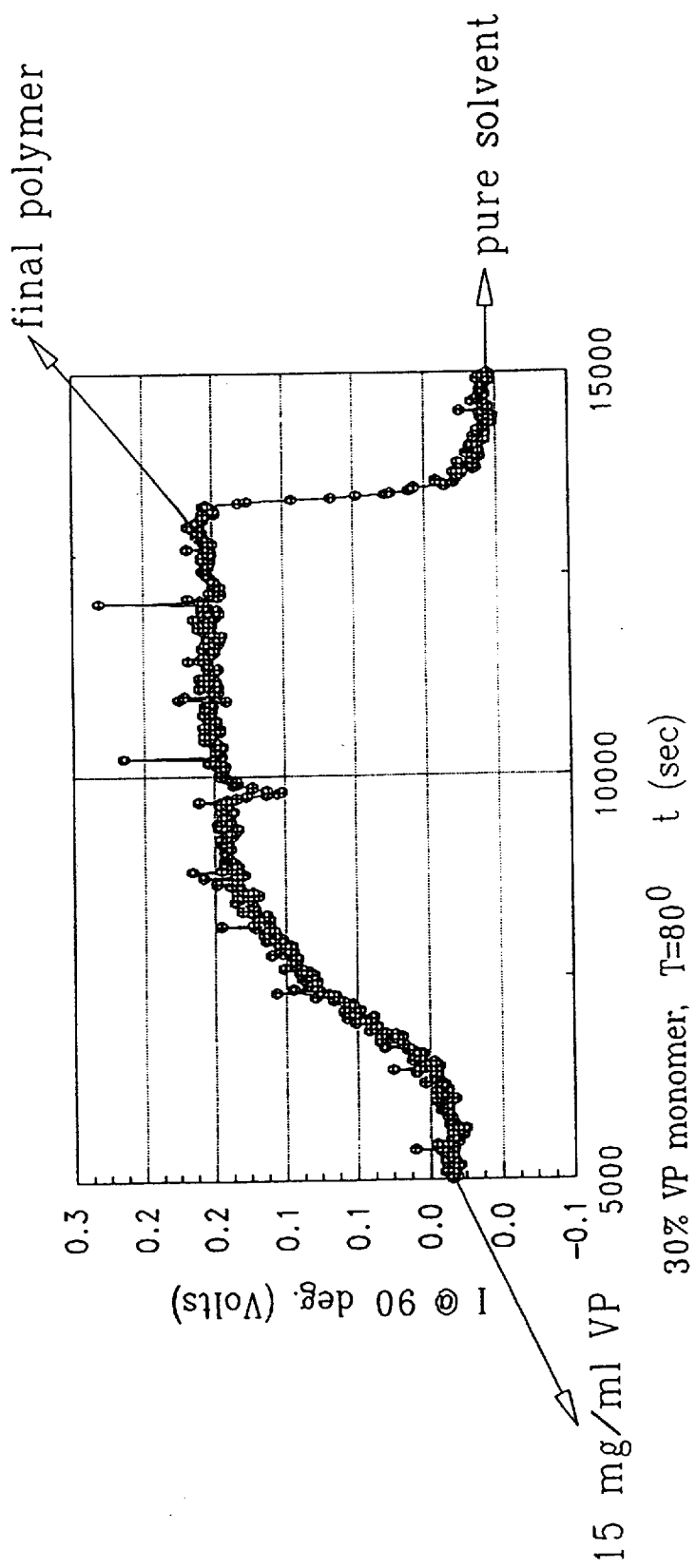
FIG. 14 shows a flow mode measurement of a polymerization reaction.

FIG. 14 shows a flow mode measurement of a polymerization reaction. Vinyl pyrrolidone monomer at 300 mg/ml at T=80° C. is polymerized using hydrogen peroxide initiator. The polymerizing mixture is withdrawn by a mixing pump, which dilutes the PVP to about 6 mg/ml. The diluted mixture is then pumped through the flow cell where the scattering is monitored continuously. Optionally, a concentration detector, such as an index of refraction detector, or ultraviolet or visible spectrophotometer, can be placed in the line of sample flow.

Figure 15:
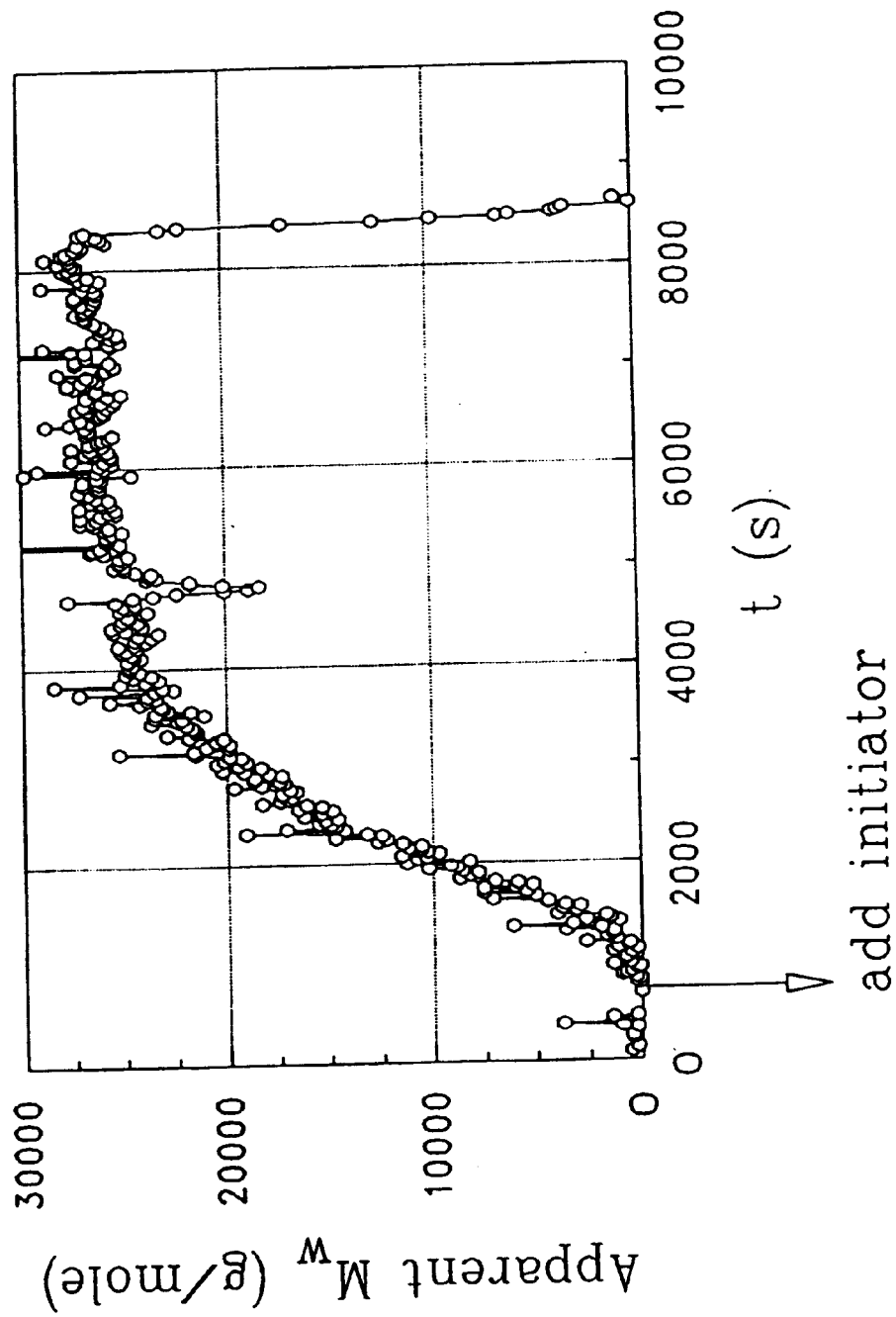
FIG. 15 shows the relative intensity converted to apparent mass (Kc/I) using equations (1)–(3), plotting approximate apparent mass versus real-time for PVP polymerization using a flow mode, using a 300 micron optic fiber at 90° and a 5 mW diode laser, and starting with 300 mg/ml VP diluted to about 6 mg/ml on-line.

FIG. 15 shows the relative intensity converted to apparent mass (Kc/I) using equations (1)–(3).

The preferred embodiment of the present invention consists of an optical assembly 20, from which a harness 43 of fiber optic cables 41 leads out detected scattered light to a remote photodetector and signal processing unit 111, 112, and optionally brings in incident light. The signal processing unit 111, 112 is itself composed of standard components such as photodiodes 118, photomultiplier tubes, amplifiers, discriminators, microcomputer 112, etc.

The optical assembly 20 preferably consists of a solid material. The minimal version consists of a ring member 21 around which the fiber optic detectors 41, incident beam input optics 31, and beam dump 32 are arrayed (see FIG. 1 for this embodiment). The optical fibers 41 are either cemented into holes 42 in the ring member 21, or are affixed with tiny optical fiber chucks (not shown), and are gathered into a ruggedized harness 43, which is led to the photodetector assembly 111, 112. The optical assembly 20 can be connected to a handle 61, which may contain a laser 62, and can be immersed directly in a sample solution 91 (see FIG. 2). The ring member 21 can also be mounted on a base plate 161. The ring member 21 can also serve as a center portion for a segmented chamber, to the endpieces 71 of which are connected hydraulic fittings 73 for fluid to be pumped in and out through in the flow mode (FIG. 3). A small baseplate 81 can be attached to the ring member assembly 20 for fill mode use (FIG. 4), or the bore 22 in the ring member assembly 20 simply need not be perforated all the way through. For insert mode, a sample vial 92 can be inserted directly into the ring member assembly 20 (FIG. 5). In cases where ambient light might give detectable interference, the ring 20 can be covered with a simple cowl or hood 114 in both immersion, fill and insert modes. In the tests presented below, ambient light was not a problem, and no cowl or covering was used.

An integral chamber version 100 (see FIG. 6) can also be made, and consists of a hollow channel or wall 101, normally cylindrical, but which may also have elliptical, square or polygonal cross section. The chief difference between the minimal ring version 20 and integral chamber version 100 is that the chamber 102 is simply longer than the ring chamber 22, so that hydraulic fittings 73 can be directly connected. Furthermore, the extra length provides additional shielding from ambient light, and no cowl or other covering should generally be needed.

In either the ring version 20 or chamber version 100, the internal diameter can be made over a wide range, depending on the application. Typically this diameter will run from about 1 mm to 20 cm. The total channel volume may range, for example, from about 3 to 50,000 microliters, with a preferred range of 10 to 1000 microliters. The wider the channel diameter the less problem there will be with stray light, but more sample solution will be required. In industrial settings, for example, where large volumes of sample are produced, and/or the samples are viscous, high volume cells may be a convenient solution, and pose the most robust and reliable means of achieving low stray light and highest ease of alignment. In situations where sample volume is scarce, e.g. in biotechnology research where only milligrams or less of substance is available, the channel will be made much narrower. Because the optical detection fibers 41 can plug into the same remote array 111 of photodetectors 118, the only change in fabrication in meeting the demands of the high sample volume vs. the low volume user is in the low cost optical probe assembly 20, 100. All photodetection, electronics, computer interfacing and basic software 111, 112 can remain the same.

In the walls of either the ring member or chamber versions, are seated an optical window 23, lens, fiber, or other component for delivering the incident beam into the channel, as well as optical fibers 41 for detection of scattered light placed at any number of scattering angles, usually from about 10° in the forward direction to about 170° in the backscattering direction. A detection fiber can also be placed at the site of the beam dump (0°). The fibers 41 can be cemented into holes 42 in the chamber 22, 102, or held in with tiny optical fiber chucks. Hence, the delivery element for the incident light and the optical fibers are in direct contact with the sample solution, or may be coated with a suitable transparent material, including glass, for protection against deleterious sample solutions. In the case for example where only a single or few angles are desired, small photodetectors (such as photodiodes) can be affixed directly to the outside wall of the chamber, thus eliminating the optical fibers 41.

The body of the optical assembly in either ring member or chamber versions can be constructed of any material suitable to withstand the nature of the sample solution, such as stainless steel, black anodized aluminum, ceramic, Teflon, nylon, polycarbonate, or other plastics. The material is preferably opaque, preferably black or blackened, to minimize glare and stray light.

The power of the incident light is arbitrary, but will typically range from 0.1 to 100 mW. For good detectability and economy, the power range will preferably be from 0.25 to 50 mW. The wavelength can likewise fall anywhere in the visible or ultraviolet range. Since there are no requirements for coherence (unless a single mode optical fiber is installed optionally to collect light for dynamic light scattering, in which case a laser light source would be required), nor does the incident light have to be extremely monochromatic (a bandwidth of 50 nm would not be excessive), the light source does not have to be a laser. As such, conventional white light, broad band, or discrete line sources, such as arc lamps, light emitting diodes, vapor lamps and incandescent sources are all possible candidates for the incident light. By the same token, if a multiple wavelength source is used, it is possible to vary the scattering vector q $$\left(q = \frac{4\pi n}{\lambda}\sin(\theta/2)\right)$$

by introducing different discrete wavelengths and detecting at a single angle; e.g. by selecting wavelengths with a monochromator in front of a white light source and introducing these into the input optics. Using light from around 200 to 800 nm could yield a factor of four variation in q. This could avoid use of multiangle detection, and require only a single fiber optic for detection and single photodetector/amplifier. On the other hand, if both multi-angle detection and multiple wavelengths are used then, say, for wavelengths from 200 to 800 nm, and scattering angles from 15° to 170°, the factor of q can be varied by as much as a factor of 30. Appropriate collimation and/or focusing optics are usually needed to introduce the source beam into the channel.

In many applications use of a laser may be preferred. A laser source would preferably be round 200–1000 nm, and more preferably 450 to 780 nm, where the majority of economical, low power, commercial lasers operate. The laser beam is preferably focused at or near the center of the hollow channel, although an uncollimated, or reduced and re-collimated beam will also work. The beam waist can range from the diffraction limit of Gaussian beams ($\lambda f/D$, where $\lambda$ is the incident wavelength, D the unfocused laser beam waist diameter and f the lens focal length) typically on the order of 1 to 200 microns, up to a 2 mm unfocused beam. The preferred beam waist diameter will depend on the intended application, and would be given as an option to a potential user of the invention, according to their needs. For example, measurement of dilute solutions of small, clean solutions would tend to use a wider beam waist, whereas concentrated solutions containing significant stray scatterers would preferably use a very highly collimated beam. Use of a highly focused beam and detectors defining a small scattering volume allows less probability of finding large particles in the scattering volume at any instant. When a large particle enters, either with the sample stationary or under flow, a large spike is produced which can then be recognized and discriminated against, in order to recover the absolute scattering from the desired scatterers. Sufficiently fast detector response allows spikes to be identified, counted (for purposes of large particle counting), and eliminated, to recover the desired background scattering.

The method of delivering the beam can be directly through an optical window on the chamber, via a tubular transfer lens, such as the endo-index type, or via an optical fiber, either flexible or rigid, with such lenses, pinholes and other light handling components as is necessary to deliver the beam in focused or collimated fashion, with the desired beam waist, and with a minimum of glare and stray light. If the beam is delivered by optical fiber, the laser can be remote from the optical assembly. Alternatively, the laser can be mounted directly to the optical assembly (FIG. 7).

Directly across from the incident beam is a beam dump 32 for the incident beam 31 to minimize 'glare' and stray light. This beam dump 32 may be of any standard type, ranging from a hole, to a 'Rayleigh horn', to a complete sub-system involving coated or un-coated lenses, and/or prisms, mirrors, a photodetector, or other optical components.

The optical fibers 41 may be of the multimode variety, whose inside diameter may range from 10 to 1000 microns, the smaller sizes being preferred where highly scattering samples are being measured, or for subsequent use with dynamic light scattering. In fact, a single, relatively large fiber diameter may be selected, such as 500 microns, and a rotatable, annular mask can be affixed to the channel wall, which would have varying diameter pinholes for defining the field of view of each optical fiber. Alternatively, the cell interior may be permanently outfitted with sets of different diameter fibers, spaced closely about each selected scattering angle, all of which could be continuously monitored. The fibers themselves can be of virtually any commercial or research grade. They must be chosen, however, so as to be compatible with the solvent and sample conditions where the invention will be applied. Where toluene is used, for example, the fibers must withstand that solvent, so glass core fibers with glass cladding and buffer would be preferred, or some similar substitute, such as glass core with CPE (chloropolysulfatal ethylene) jacket from Belden corporation.

The way the optical fibers 41 are attached to the cell 21, 101 helps to define the scattering volume. If the fibers reach through the cell to the surface of the channel (chamber) 22 102, then the scattering angle will be defined by both the acceptance angle of the fiber in the particular solvent the cell contains, and the beam waist. Definition of the scattering volume in this way can be termed the 'fiber acceptance angle mode'. If the fiber 41 is recessed back into a hole 42 in the chamber to the point where the angle subtended by the two ends of the cylindrical hole 42 is less than the acceptance angle of the fiber 41, then detection can be said to be in the 'pinhole mode'. The difference in detection modes is shown schematically in FIGS. 8 and 9.

The optical harness 43 leads all the detection fibers to a remote bank 111 of photodetectors 118. The fibers 41 can be coupled to their respective detectors 118 by inserting them into permanently aligned quick connect optical fiber connectors, as are commercially available (e.g. Newark Corp. or Amphenol Corp.), positioned in front of the detector surfaces.

The optical assembly can be used in several modes. In one of its submersible modes, the assembly 20, with no additional modifications, can be directly submerged into a sample solution 91 contained in a test tube 92, industrial tank, etc. As a remote, fill mode unit, the channel may be capped at one end (or the channel simply does not have to be bored completely through), which allows a small quantity of sample to be pipetted, scooped, or otherwise introduced into it and reside in it, remotely from the main sample supply, if desired. Each end of the channel may also be outfitted with a coupling to accept a fluid flow, so that the assembly may also be used in flow mode, such as for monitoring, optionally with on-line dilution, unfractionated polymers degraded or produced in a vat, fractionated polymers from Size Exclusion Chromatography, capillary hydrodynamic fractionation, etc. In this mode of operation it may be desirable to hydrodynamically taper the interior to optimize the flow past the plane of the optical fibers and incident beam. The invention can also be used in insert mode, whereby samples in sealed cells or vials can simply be inserted into the ring member or chamber, in the traditional fashion. In this case, one returns to the common situation in which there is a transparent cell, between the sample, incident beam and detection optics.

The invention can be simultaneously cleaned and absolutely calibrated by use of an appropriate solvent such as toluene, whose absolute Rayleigh scattering ratio is known. The probe is immersed in the solvent, or the solvent made to flow through it for cleaning purposes. At the same time, the solvent scattering is monitored, and when it reaches a steady value, this is used for determination of the absolute calibration factors for each detection fiber.

As regards the minimal ring member version, it can be used submersibly on its own or become a central portion of a three piece unit. This may be desirable for purposes where quick interchange of optical assemblies to different specifications, cleaner or newer units are made, etc.

In both the ring member version 20 and integral chamber version 100, an outer protective sheathing 45, such as a ring member of plastic or metal may slip over the fiber optics 41 protruding externally from the ring member 21 or chamber wall 101. Likewise in all cases, the entire optical assembly, whether a ring member or chamber, can be placed within a completely enclosed housing, into which sample can be introduced either by flow or immersion. Such a housing may be desirable when the optical assembly needs special protection from a harsh (e.g. high temperature) environment, or is immersed in turbulent or otherwise potentially damaging or signal distorting liquids.

The present invention includes the aforementioned ring member or integral chamber SLS probe. The incident beam 31 is introduced into the device via optical window 23, or a fiber optic and/or tubular lens and other optical elements, and scattered light is taken out via fiber optics 41 whose tips 44 are arrayed at various angles in the horizontal plane of the ring member 21 or chamber wall 101. All the optical fibers 41 and elements are drawn together into an 'optical harness' 43, which is led to the 'outside world' through a hollow handle 61 on the device 20. The optical fibers 41 carrying scattered light and issuing from the harness 43 are coupled to conventional optical detectors 118 (e.g. PIN or avalanche photodiodes, photo multiplier tubes, etc.) whose voltage or current signals are led to a conventional signal processing device and/or into a computer 112. The optical probe portion consists essentially of a piece of material, preferably dark, with optical fibers and a few other inexpensive optical elements (such as borosilicate windows 23) attached into a harness. As such, the probe itself should be quite inexpensive and could even be disposable. The photodetectors 118, signal processing and computer analysis portions of the instrument are remote and permanent (although quite portable), and represent the major cost. In some cases, especially where few angles are involved, and submersible operation is not a priority, photodetectors (e.g. photodiodes) can be mounted directly to the chamber, thus avoiding use of the fiber optic detectors.

In the submersible mode, calibration (and cleaning) can be done by merely immersing the probe in a calibration solvent, kept handy in a closed vessel. This could be toluene, or any other solution whose absolute Rayleigh scattering ratio is known.

The software in Appendix A can serve as a basis for data reduction, analysis and display. Data can be collected and reduced either on a standard microcomputer, or by building a customized microprocessor based unit. The software ican include programmed criteria for averaging scattering signals, identifying, counting and rejecting scattering spikes from large, stray scatterers, and informing the operator when signal collection is done. Software can access on-board libraries to inform the operator of likely phenomena occurring in the sample (e.g. aggregation, gelation, degradation), and problems such as poor solution quality (e.g. too much 'dust'), presence of aggregates, or other anomalies.

Experimental Verifications of the Invention

I) Fill mode tests:

A) Transfer lens version/single angle

A first prototype of the invention in the integral chamber version was made in order to assess whether absolute macromolecular characterization, in terms of molecular mass, was feasible. This is meant to be only a demonstration of the feasibility of the invention, not a highly precise absolute molecular mass determination nor critical comparison of the inventions performance with a commercial instrument.

Dextran of nominal mass 200,000–300,000 g/mole was selected for the measurement. It was mixed at 0.003 g/cm$^3$ in an aqueous solvent containing 0.1 Molar $NH_4NO_3$ and 0.1% sodium azide for protection against bacterial contamination. There is nothing special about this particular solvent, and even pure water would have been adequate (since dextran is a neutral polymer and is not subject to the unusual physical effects that charged polymers display in pure water).

An optical unit was fabricated from a 1⅞" inch long piece of, e.g., black nylon round stock of ⅝" o.d. An inner, cylindrical channel of diameter 7.7 mm was bored concentric with the axis. The inner ends of the channel were tapped to accommodate standard ⅜" plugs, barbs and other hydraulic fittings. Perpendicular to the cylinder axis, a hole was drilled to accommodate a 1.98 mm o.d. Endogrins® lens, obtained from Edmund Scientific Co. Straight across from this hole on the opposite side of the channel a larger diameter hole was drilled for use as a beam dump. At 90° to the incident light hole a small hole was drilled to accommodate an optical fiber with inner core 100 microns and cladding 140 micron o.d. The fiber was inserted into the hole in the channel, and was found to work best when protruding but slightly from the hole into the channel. Both the fiber and lens were secured in their holes with optical putty. The opposite end of the fiber, which was about two feet long, was secured remotely from the optical assembly into a fiber optic chuck from New Focus Co., and butted up against the photosensitive surface of a Hammamatsu photodiode with integral FET op-amp, contained inside a light-tight box, containing both the diode/FET and an additional standard operational amplifier stage.

The amplified signal was fed into a Nicolet 4094B digitizing oscilloscope, although any data collection device with a rate of 1 KHz or faster would have sufficed. Sampling at 1 KHz or faster allows spikes from diffusing impurity particles and fluctuating scattering levels to be recognized and rejected, leaving the desired signal from the polymer or colloid scatterers. In fact, spike and fluctuation rejection was used in this and other tests.

Light of wavelength 488 nm and approximately 20 mW was from a Coherent Corp. Argon ion laser, which had an output beam waist of about 2 mm. The light could be delivered either highly focused or uncollimated. For high focusing, a 5 mm lens with a focal length, f=5 mm from Edmund Scientific was placed external to the optical assembly, and led to a beam waist of about 1.5 microns. This was transferred into the channel of the optical assembly via the 1.98 mm Endogrins® lens, which was 6 cm long. Alignment of the delivered beam with respect to the detection fiber optic at 90°, and signal maximization for this arrangement was achieved by using a solution consisting of a 1/40 dilution of 190 Angstrom latex spheres from Duke Scientific, although any moderately scattering solution, such as water with a tiny drop of milk or coffee creamer powder, would be adequate.

The system was then tested by measuring, sequentially, the photodiode dark count (i.e. with no laser beam entering the optical assembly), the photovoltage with pure water, with a 3 mg/ml solution of dextran, and toluene. The various liquids were introduced into and removed from the cell with a long, glass pipette with a rubber suction bulb at one end. The photovoltages are listed below:

Table of Photovoltages (accuracies are to about +/−1 mV)

| measured | volt. (mV) | scattering difference | K | Rayleigh ratio, I (cm$^{-1}$) | Kc/I | app. M (θ = 90°) | app. M Wyatt Dawn F (θ = 144°)** |
|---|---|---|---|---|---|---|---|
| Photodiode dark voltage | −65 | NA | NA | NA | NA | NA | NA |
| pure water | −57 | NA | NA | NA | NA | NA | NA |
| 3 mg/ml dextran | −30 | $I_{dex}-I_{water}$ = 27 | 1.46 × 10$^{-7}$ | 7.63 × 10$^{-5}$ | 4.23 × 10$^{-6}$ | 174,000 | 191,000 |
| toluene dn/dc = 0.142 for dextran | −51 | $I_{tol}-I_{dark}$ = 14 | NA | 3.96 × 10$^{-5}$* | NA | NA | NA |

*This is the known Rayleigh ratio for toluene at T = 25° C. for λ = 488 nm.
**This is the proper angle for comparison, since the Dawn-F was used with a 632 nm He—Ne laser, and the test chamber with a 488 nm Argon ion laser.

The Zimm equation for SLS, when $q^2<S^2><<1$ is $$\frac{Kc}{I} = \frac{1}{M_{app}} = \frac{1}{M_w}\left(1 + \frac{q^2<S^2>_z}{3}\right) + 2A_2c \quad (1)$$

where I is the excess Rayleigh scattering ratio from the polymer solution (the total scattering minus the pure solvent background). $M_{app}$ is the apparent mass, defined as per the equation (i.e. it neglects the effects of finite $2A_2c$ and $<S^2>_z$ effects). $M_w$ is the weight averaged polymer mass, $<S^2>_z$ is the z-averaged radius of gyration, $A_2$ is the second virial coefficient, c is the polymer concentration in g/cm$^3$, and K is given, for vertically polarized light, $$K = \frac{4\pi^2 n^2 (dn/dc)^2}{N_A \lambda^4} \quad (2)$$

where n is the index of refraction of the sample solvent (n=1.33 for water), and $\lambda=4.88\times 10^{-5}$ cm is the vacuum wavelength of the incident light.

The absolute scattering I was calculated according to $$I(q) = \frac{V(q) - V_s(q)}{V_c(q) - V_d(q)} I_c f \quad (3)$$

where V(q) is the photodetector voltage from the sample scattering at wave vector q, $V_s(q)$ is the scattering voltage at q of the pure solvent in which the polymer or colloid is dissolved, $V_c(q)$ is the scattering voltage of the calibration solvent scattering at q, and $V_d(q)$ is the, dark voltage of the photodetector at q. $I_c$ is the known, absolute Rayleigh scattering ratio for the calibration solvent. For toluene at 25° C., $I_c=1.406\times 10^{-5}$ cm$^{-1}$ at 633 nm, and $4.96\times 10^{-5}$ cm$^{-1}$ at 488 nm. In equation 3, f is an optical correction factor, given approximately as $(n_{sample\ solvent}/n_{calibration\ solvent})^3$. This accounts approximately for the difference in field of view and detector solid angle for optical fibers in the chamber. For water n=1.333 and for toluene n=1.494 so that f is approximately 0.71.

The results for the dextran are shown in the above table. The apparent, mass of 174,000 (at θ=90°) is obtained from the invention and 191,000 from the Wyatt Dawn F (at θ=144°). At these angles, $q^2$ is approximately the same for each instrument. At any rate, $R_g=225$ Angstroms for this Dextran (as measured on the Dawn F), so that there is very little $q^2$ dependence over the visible light range.

The fact that the apparent mass from the invention is within 10% of the value of that obtained from an established instrument clearly demonstrates the feasibility of making absolute molecular mass determinations. Refinement of the instrumentation should make results even more accurate. At any rate, it is generally recognized in the SLS field that molecular weights of polydisperse samples are seldomly accurate to more than a few percent.

B) Multiple angles

A similar chamber (with no hydraulic fittings) was made except that ii was outfitted with detection fibers at 70°, 90° and 135°, and two opposed 3 mm sapphire windows, glued into holes in the chamber, were used for beam ingress and egress. Toluene was used for absolute calibration at each angle. Zimm plot results from a solution of high molecular weight PVP are shown in FIG. 10. Ten mW of argon ion laser power were used, and a 50 nm focal length lens was used to focus the laser beam through the window in the chamber.

II. Immersion mode test:

An immersion cell was constructed from nylon roundstock of 16 mm outer diameter and 12 mm i.d. and 8 mm long. 150 micron optical fibers were glued in with epoxy at 45°, 90° and 150°, with their front surfaces at the level of the inner cell diameter face. Two 3 mm holes were cut in opposite ends of the cylinder, and were left empty for the tests (i.e. neither entrance window nor beam dump were used). The optical fibers leading to the remote detector were secured so that no additional bending or deformation of them occurred, since additional bending or deforming leads to large losses in transmitted light. A tubular stainless steel handle was attached to the cylinder to allow for manipulation. The cylinder was immersed in 3" diameter beakers containing the test liquids, and the handle, protruding from the solution, was secured with a ringstand. 20 mW of Argon ion laser power were delivered in a beam from above the beakers, and a 50 mm focal length lens was used to focus the light in the center of the cylindrical chamber.

Scattering tests at the three angles were carried out using 0.2, 1.0, 1.5 and 2.0 mg/ml solutions of a high molecular weight polymer, PVP. A digitizing oscilloscope was again used to monitor the detected light at each angle, one at a time. These solutions were unfiltered. Identification and rejection of spikes from large impurity particles diffusing through the scattering volume and fluctuating signals from other causes allowed this unusual series of measurements on unfiltered solutions to be made. The scattering voltage of toluene at each angle was used to find the absolute calibration factor at each angle. FIG. 11 shows typical results. These compare quite favorably with the results for the fill mode example above (I-B).

III. Flow mode tests

A 3-piece flow cell was constructed out of nylon roundstock of 16 mm o.d. The central portion was 8 mm long, with a 7 mm bore, and contained a single 300 micron fiber epoxied in at a scattering angle of 90°. Two 3 mm sapphire windows were mounted on opposite sides of the central bore, one for laser beam ingress, the other for egress. Endcaps of the same material and o.d. pressed on each side of the central portion and O-rings created a seal. Round aluminum plates outfitted with long bolts served to clamp the endcaps to the central piece. The endcaps each had a small hole drilled in them for fluid to reach the bore of the central portion, and each was outfitted with a standard GPC fitting, allowing attachment of standard PEEK (polyethyleneethyleneketone) HPLC (high performance liquid chromatography) tubing to allow liquid samples to be pumped in and out.

The basic construction of the center portion can be identical to that of the immersion cell, making the two ultimately interchangeable, or at least slight modular variations of each other. Also, these cells can easily become fill mode cells by simply adding a base plate (as in the drawings).

A) Debye plot at a single angle

Solutions of high molecular weight PVP of concentrations 0.25, 0.5, 1.5 and 2.0 mg/ml were pushed through the cell manually with a syringe, at roughly 1 ml/min. The experiment was repeated several times and error bars obtained. Kc/I at θ=90° is shown in FIG. 12, along with the associated error bars, and a comparison with results from a Wyatt Dawn-F. Ten mW of argon ion laser power were used, and a 50 mm focal length lens was used to focus the laser beam through the window in the chamber.

B) Discrimination against large particles

The present inventor wrote program REEDFLO (see Appendix A) to capture data through a DT2801-a analog-to-digital converter board and perform averaging and data storage functions. Maximum speed is about 40 microseconds per point with this board, and up to eight separate detectors can be monitored per board in the differential input mode. The idea was first tested as to whether the flow cell with small scattering volume could usefully measure both absolute polymer scattering levels and identify and count spikes from large particles. Ten mW of argon ion laser power were used, and a 50 mm focal length lens was used to focus the laser beam through the window in the chamber. The scattering volume was roughly $5 \times 10^{-7}$ cc.

To this end a mixture of 0.5 mg/ml PVP of molar mass around $10^6$ grams/mole was mixed with Duke Scientific 10 micron latex spheres such that the sphere concentration was $4 \times 10^4$ particles per cc. This gave roughly an average of 0.02 particles per scattering volume. The solution was pushed through the cell manually using a syringe, roughly at a flow rate of 1 ml/minute. The 5 mW diode laser (wavelength=635 nm) was used as the light source.

FIG. 13 shows that the cell was capable of measuring both the homogeneous background scattering from the polymers, and both identify and count the number of large particles in the flowing sample. Given the pure solvent level shown on the drawing, it is hence possible to recover the absolute intensity scattered by the homogeneous polymer background scattering. A significant degree of contamination by large particles can hence be tolerated in this system.

C) Kinetics of Polymerization

The kinetics of polymerization were carried out in real-time using the flow cell. A 5 mW diode laser was used, and a 50 mm focal length lens was used to focus the laser beam through the window in the cell. A 30% solution of vinyl pyrrolidone (VP) monomer was mixed in water with 0.1% ammonia, and the solution heated to 80° C. The polymerization was initiated with 0.7% hydrogen peroxide. At high concentrations, such as 30% VP, there is very little change in light scattering intensity as polymerization proceeds (i.e. in eq. (1) $2A_2c$ is much larger than $1/M_w(1+q^2<S^2>_z/3)$. Hence the reaction solution must be diluted for TDSLS to be a useful monitor of $M_w$ in real-time. To do this, concentrated reactant is withdrawn with a pump and mixed with solvent from a separate reservoir of pure solvent. This can be achieved by using a hydraulic 'T' one arm of which goes to the concentrated reaction solution, and the other to the pure solvent, with the mixed output being then pumped out by a pump and forced through the scattering flow chamber. It turned out that use of a programmable mixer was more convenient for mixing reactant and pure solvents. A standard ISCO (corporation) 2350 HPILC pump was used to pull mixed material from this pump and push it through the flow cell and refractive index (RI) detector, which was placed in series with the flow to measure the concentration, and any possible variations, of the diluted sample. For this experiment the reaction mixture, initially at 30% VP, was diluted so that the sample passing through the flow chamber was it 6 mg/ml.

FIG. 14 shows the results of a polymerization reaction in terms of scattered intensity in arbitrary units vs. time, whereas FIG. 15 shows the approximate apparent mass, obtained by eqs. (1)–(3). The apparent mass is simply I/Kc. For PVP of mass about 30 kD, there is no significant angular dependence, so $q^2<S^2>\sim 0$. Furthermore, $A_2 \sim 5 \times 10^{-4}$ so that at a PVP concentration of 0.006 g/cm$^3$, $2A_2cM_w \sim 0.18$. Such a correction to the apparent mass, about 18%, is easily taken into account.

Table of Abbreviations $A_2$=second virial coefficient (cm$^3 \times$Mole/g$^2$)
C=concentration (in g/cm$^3$)
g/cm$^3$=grams per cubic centimeter
g/mole=gram per mole
FET=field effect transistor
He—Ne laser=Helium Neon laser
HPLC=High Pressure Liquid Chromatography
kD=kiloDalton (1,000 grams per mole)
$\lambda$=wavelength
$M_w$=weight average molecular mass (grams per mole)
mg/ml=milligram per milliliter
ml=milliliter
ml/min=milliliter per minute
mV=millivolt
mW=milliwatt
nm=nanometer
PVP=poly(vinyl pyrrolidone)
$<S^2>$=mean square radius of gyration (in Angstrom$^2$, nm$^2$, or cm$^2$)
SEC=Size Exclusion Chromatography
SLS=Static light scattering
TDSLS=Time dependent static light scattering
VP=vinyl pyrrolidone

PARTS LIST:

The following is a list of parts and materials suitable for use in the present invention:

| | |
|---|---|
| 10 | optical assembly of the preferred embodiment of the present invention |
| 20 | ring member assembly of a first embodiment of the present invention |
| 21 | ring member of the ring member assembly 20 of the first embodiment of the present invention (such as nylon, polycarbonate, anodized aluminum, kevlar or ceramic) |
| 22 | chamber of ring member 21 |
| 23 | incident beam window of ring member 21 (e.g. Edmund scientific borosilicate or sapphire circular windows) (e.g., 5 mm diameter, 2 mm thick) |
| 24 | beam dump window of ring member 21 (same as 23, or similar) |
| 31 | incident beam (provided by, for example, a vertically polarized 5 mW diode laser commercially available from Lasermax Inc., Rochester, NY) |
| 32 | beam dump (such as a window or prism followed by a Rayleigh horn or a detection fiber) |
| 41 | optical fibers (such as optical fibers of 100, 150 and 300 micron core diameter, commercially available from Polymicro Technologies as parts FVP100110125, FVP150165180 and FVP300330370, respectively.) |
| 42 | holes for optical fibers 41 |
| 43 | optical harness (e.g. the fibers can be 'braided' together with semiflexible plastic tubes and covered with a rugged sheath, such as is commonly done for telecommunication fiber bundles) |
| 44 | ends of the optical fibers 41 |
| 45 | outer protective sheathing |
| 51 | sample solution (for example 1 mg/ml Polyvinylpyrrolidone in water) |
| 52 | container for sample solution 51 (glass beaker, for example) |
| 61 | handle for ring member assembly 20 (stainless steel, for example) |
| 62 | light source (such as a diode laser) |
| 63 | converging lens |
| 70 | flow mode assembly of the present invention |
| 71 | end piece of flow mode assembly 70 (made of nylon, ceramic, anodized aluminum, or kevlar, for example) |
| 72 | hydrodynamic tapered flow channels in end pieces 71 |
| 73 | HPLC tubing and fittings (e.g. Rainin Corp., or ISCO) |
| 74 | O-rings |
| 75 | retaining bolts |
| 80 | fill mode assembly of the present invention |
| 81 | base plate (made of plastic or anodized aluminum, for example) |
| 91 | sample solution (1 mg/ml polyvinylpyrrolidone in water, for example) |
| 92 | container for sample solution 91 (glass, for example) |
| 100 | integral chamber assembly of the present invention |
| 101 | integral chamber wall (such as stainless steel, black anodized aluminum, ceramic, Teflon, nylon, polycarbonate, or other plastics) |
| 102 | integral chamber |
| 111 | photodiode assembly (containing Hammamatsu Corp photodiodes, for example) |

-continued

PARTS LIST:

| | |
|---|---|
| 112 | computer for data collection and analysis (such as an IBM personal computer clone such as a Starion 919 from Digital Equipment Corp.) |
| 113 | strain relief loop |
| 114 | cowl |
| 115 | acceptance angle of fiber optic 41 in FIG. 8 |
| 116 | acceptance angle of fiber optic 41 in FIG. 9 in water |
| 117 | acceptance angle of fiber optic 41 in FIG. 9 in toluene |
| 118 | optical detectors |
| 161 | base plate |

REFERENCES (INCORPORATED HEREIN BY REFERENCE)

1. Zimm, B. H. J. Chem. Phys., 16, 1093–1116 (1948)
2. W. F. Reed "Time-dependent light scattering from singly and multiply stranded linear polymer undergoing random and endwise scission", J. Chem. Phys., 103, 7576–7584. (1995)
3. S. Ghost and W. F. Reed "New Light Scattering Signatures from Polymers undergoing Depolymerization w. App. to Proteoglycan Degradation" Biopolymers, 35, 435–450 (1995)
4. W. F. Reed "Time-Dependent Processes in Polyelectrolyte Solutions ", invited chapter for Berichte der Bunsen-Gesellschaft special volume on Polyelectrolytes, 100, 6, 1–11, 1996

All measurements disclosed herein are at standard temperature and pressure, at sea level on Earth, unless indicated otherwise. All materials used or intended to be used in human being are biocompatible, unless indicated otherwise.

Attached as Appendix A is data collection and storage software which can be used as a basis for more complex software to perform absolute macromolecular characterization and electronically filter out, count, and characterize large scattering particles.

As used herein, "large scattering particle" (LSP) means an individual particle which would produce scattered light greater than the noise level of the detector (in FIG. 13, for example, the noise level is around 0.04V and the large scattering particles are indicated at about 12 seconds, 26 seconds, 38 seconds, and 46 seconds, in addition to other locations). A LSP could be unwanted impurities, aggregates of the polymer or colloid being studied, or an integral part of the solution.

The detectors and interface operate at a rate fast enough to resolve the residence time of a large scattering particle in the scattering volume. The interface between the photodetector and the computer can be a voltage-converting or a current-converting interface.

Preferably, the scattering volume is chosen such that the number of large scattering particles is small enough to not prevent absolute macromolecular characterization of the substance being studied, and preferably small enough to not significantly interfere with absolute macromolecular characterization of the substance being studied. For example, the average number of LSPs in the scattering volume can be less than 1000, preferably less than 500, more preferably less than 200, even more preferably less than 100, still more preferably less than 50, even more preferably less than 20, even more preferably less than 10, most preferably less than 5. The average number of LSPs in the scattering volume can be even 0 to 1.

The present invention is a relatively inexpensive, simple, versatile apparatus for use in SLS and TDSLS.

The size range of detectability can be, for example, 20 Angstroms to 100 microns. The size range of detectability should run from about 20 Angstroms to 100 microns, with useful measurability in the range from 20 Angstroms to 2 microns, and a preferred range from about 20 Angstroms to 5000 Angstroms. Stated in terms of molar mass, the detectable range of particles should run from about 500 g/mole to $10^{14}$ g/mole, with useful measurability in the range of 500 g/mole to $10^9$ g/mole, with a preferred range from about 1000 g/mole to $10^7$ g/mole.

The transmission means for transmitting light from the light detection means to the photodetectors is preferably of a sufficient length and flexibility to allow the submersible probe to be submersed in the fluid to be sampled without submersing the photodetectors, and to allow the other probes to be remote from the photodetectors, which is helpful when the probe is to be used in harsh environments which might damage the photodetectors and associated electronics.

As used in the claims, "light source" can refer to a window, lens, or optical fiber, for letting light in from a light generator, such as a laser.

The foregoing embodiments are presented by way of example only; the scope of the present invention is to be limited only by the following claims.

I claim:

1. Apparatus for static light scattering for absolute macromolecular characterization, comprising:
   a submersible probe for use with at least one photodetector and a computer electronically connected to the photodetector, the computer being programmed for analyzing data from static light scattering for performing absolute macromolecular characterization, the probe being submersible in a fluid to be sampled, the probe comprising:
   a light source;
   light detection means secured in a fixed position relative to the light source;
   transmission means for transmitting light from the light detection means to the photodetector, the transmission means being of a sufficient length and flexibility to allow the submersible probe to be submersed in the fluid to be sampled without submersing the photodetector.

2. The apparatus of claim 1, further comprising the photodetector and the computer.

3. The apparatus of claim 1, comprising a plurality of photodetectors.

4. The apparatus of claim 1, wherein the probe comprises:
   a ring member having a channel into which sample fluid enters upon immersion;
   means for securing the light source in the ring member; and
   means for securing the light detection means in the ring member.

5. Apparatus for static light scattering for absolute macromolecular characterization, comprising:
   a submersible probe for use with at least one photodetector and a computer electronically connected to the photodetector, the computer being programmed for analyzing data from static light scattering for performing absolute macromolecular characterization, the probe being submersible in a fluid to be sampled, the probe comprising:
   a light source;
   light detection means secured in a fixed position relative to the light source;

transmission means for transmitting light from the light detection means to the photodetector, the transmission means being of a sufficient length and flexibility to allow the submersible probe to be submersed in the fluid to be sampled without submersing the photodetector, wherein the probe comprises:

a ring member having a channel into which sample fluid enters upon immersion;

means for securing the light source in the ring member; and means for securing the light detection means in the ring member, wherein the ring member includes a beam dump.

6. Apparatus for static light scattering for absolute macromolecular characterization, comprising:

a submersible probe for use with at least one photodetector and a computer electronically connected to the photodetector, the computer being programmed for analyzing data from static light scattering for performing absolute macromolecular characterization, the probe being submersible in a fluid to be sampled, the probe comprising:

a light source;

light detection means secured in a fixed position relative to the light source;

transmission means for transmitting light from the light detection means to the photodetector, the transmission means being of a sufficient length and flexibility to allow the submersible probe to be submersed in the fluid to be sampled without submersing the photodetector, wherein the probe comprises:

a ring member having a channel into which sample fluid enters upon immersion;

means for securing the light source in the ring member; and means for securing the light detection means in the ring member, wherein the ring member is made of an opaque material.

7. The apparatus of claim 1, wherein the light detection means comprises fiber optic light conduits.

8. Apparatus for static light scattering for absolute macromolecular characterization, comprising:

a submersible probe for use with at least one photodetector and a computer electronically connected to the photodetector, the computer being programmed for analyzing data from static light scattering for performing absolute macromolecular characterization, the probe being submersible in a fluid to be sampled, the probe comprising:

a light source;

light detection means secured in a fixed position relative to the light source;

transmission means for transmitting light from the light detection means to the photodetector, the transmission means being of a sufficient length and flexibility to allow the submersible probe to be submersed in the fluid to be sampled without submersing the photodetector, and means for removably attaching the light transmission means to the photodetector.

9. Apparatus for static light scattering for absolute macromolecular characterization, comprising:

a submersible probe for use with at least one photodetector and a computer electronically connected to the photodetector, the computer being programmed for analyzing data from static light scattering for performing absolute macromolecular characterization, the probe being submersible in a fluid to be sampled, the probe comprising:

a light source;

light detection means secured in a fixed position relative to the light source;

transmission means for transmitting light from the light detection means to the photodetector, the transmission means being of a sufficient length and flexibility to allow the submersible probe to be submersed in the fluid to be sampled without submersing the photodetector, and a harness for securing the light transmission means to minimize damage to the light transmission means.

10. Apparatus for static light scattering for absolute macromolecular characterization, comprising:

a photodetector;

a computer electronically connected to the photodetector, the computer being programmed for analyzing data from static light scattering for performing absolute macromolecular characterization, a submersible probe for use with the photodetector and the computer, the probe being submersible in a fluid to be sampled, the probe comprising:

a light source;

light detection means secured in a fixed position relative to the light source;

transmission means for transmitting light from the light detection means to the photodetector, the transmission means being of a sufficient length and flexibility to allow the submersible probe to be submersed in the fluid to be sampled without submersing the photodetector, wherein the size range of detectability is about 20 Angstroms to about 100 microns.

11. Apparatus for static light scattering for absolute macromolecular characterization, comprising:

a photodetector;

a computer electronically connected to the photodetector, the computer being programmed for analyzing data from static light scattering for performing absolute macromolecular characterization, a submersible probe for use with the photodetector and the computer, the probe being submersible in a fluid to be sampled, the probe comprising:

a light source;

light detection means secured in a fixed position relative to the light source;

transmission means for transmitting light from the light detection means to the photodetector, the transmission means being of a sufficient length and flexibility to allow the submersible probe to be submersed in the fluid to be sampled without submersing the photodetector, wherein the detectable range of particle molar masses is from about 500 g/mole to about $10^4$ g/mole.

12. Apparatus for static light scattering, comprising:

a submersible probe for use with at least one photodetector and a computer electronically connected to the photodetector, the computer being programmed for analyzing data from static light scattering for performing characterization of a fluid, the probe being submersible in a fluid to be sampled, the probe comprising:

a ring member;

a light source secured in the ring member;

light detection means secured in the ring member in a fixed position relative to the light source;

transmission means for transmitting light from the light detection means to the photodetector, the transmission means being of a sufficient length and flexibility to allow the submersible probe to be submersed in the fluid to be sampled without submersing the photodetector.

13. The apparatus of claim 12, further comprising the photodetector and the computer.

14. The apparatus of claim 12, comprising a plurality of photodetectors.

15. The apparatus of claim 12, wherein the probe comprises:

a ring member having a channel into which sample fluid enters;

means for securing the light source in the ring member; and means for securing the light detection means in the ring member.

16. Apparatus for static light scattering, comprising:

a submersible probe for use with at least one photodetector and a computer electronically connected to the photodetector, the computer being programmed for analyzing data from static light scattering for performing characterization of a fluid, the probe being submersible in a fluid to be sampled, the probe comprising:

a ring member;

a light source secured in the ring member;

light detection means secured in the ring member in a fixed position relative to the light source;

transmission means for transmitting light from the light detection means to the photodetector, the transmission means being of a sufficient length and flexibility to allow the submersible probe to be submersed in the fluid to be sampled without submersing the photodetector wherein the probe comprises:

a ring member having a channel into which sample fluid enters;

means for securing the light source in the ring member; and means for securing the light detection means in the ring member, wherein the ring member includes a beam dump.

17. Apparatus for static light scattering, comprising:

a submersible probe for use with at least one photodetector and a computer electronically connected to the photodetector, the computer being programmed for analyzing data from static light scattering for performing characterization of a fluid, the probe being submersible in a fluid to be sampled, the probe comprising:

a ring member;

a light source secured in the ring member;

light detection means secured in the ring member in a fixed position relative to the light source;

transmission means for transmitting light from the light detection means to the photodetector, the transmission means being of a sufficient length and flexibility to allow the submersible probe to be submersed in the fluid to be sampled without submersing the photodetector wherein the probe comprises:

a ring member having a channel into which sample fluid enters;

means for securing the light source in the ring member; and means for securing the light detection means in the ring member, wherein the ring member is made of an opaque material.

18. The apparatus of claim 12, wherein the light detection means comprises fiber optic light conduits.

19. Apparatus for static light scattering, comprising:

a submersible probe for use with at least one photodetector and a computer electronically connected to the photodetector, the computer being programmed for analyzing (lata from static light scattering for performing characterization of a fluid, the probe being submersible in a fluid to be sampled, the probe comprising:

a ring member;

a light source secured in the ring member;

light detection means secured in the ring member in a fixed position relative to the light source;

transmission means for transmitting light from the light detection means to the photodetector, the transmission means being of a sufficient length and flexibility to allow the submersible probe to be submersed in the fluid to be sampled without submersing the photodetector, and means for removably attaching the light transmission means to the photodetector.

20. Apparatus for static light scattering, comprising:

a submersible probe for use with at least one photodetector and a computer electronically connected to the photodetector, the computer being programmed for analyzing data from static light scattering for performing characterization of a fluid, the probe being submersible in a fluid to be sampled, the probe comprising:

a ring member;

a light source secured in the ring member;

light detection means secured in the ring member in a fixed position relative to the light source;

transmission means for transmitting light from the light detection means to the photodetector, the transmission means being of a sufficient length and flexibility to allow the submersible probe to be submersed in the fluid to be sampled without submersing the photodetector, and a harness for securing the light transmission means to minimize damage to the light transmission means.

21. Apparatus for static light scattering, comprising:

a photodetector;

a computer electronically connected to the photodetector, the computer being programmed for analyzing data from static light scattering for performing characterization of a fluid, a submersible probe for use with the photodetector and the computer, the probe being submersible in a fluid to be sampled, the probe comprising:

a ring member;

a light source secured in the ring member;

light detection means secured in the ring member in a fixed position relative to the light source;

transmission means for transmitting light from the light detection means to the photodetector, the transmission means being of a sufficient length and flexibility to allow the submersible probe to be submersed in the fluid to be sampled without submersing the photodetector, wherein the size range of detectability is about 20 Angstroms to about 100 microns.

22. Apparatus for static light scattering, comprising:

a photodetector;

a computer electronically connected to the photodetector, the computer being programmed for analyzing data from static light scattering for performing characterization of a fluid, a submersible probe for use with the photodetector and the computer, the probe being submersible in a fluid to be sampled, the probe comprising:

a ring member;

a light source secured in the ring member;

light detection means secured in the ring member in a fixed position relative to the light source;

transmission means for transmitting light from the light detection means to the photodetector, the transmission means being of a sufficient length and flexibility to allow the submersible probe to be submersed in the fluid to be sampled without submersing the photodetector, wherein the detectable range of particle molar masses is from about 500 g/mole to about $10^{14}$ g/mole.

23. Apparatus for static light scattering, comprising:

a plurality of interchangeable probes for use with at least one light detector and a computer electronically connected to the photodetector, the computer being programmed for analyzing data from static light scattering for performing characterization of a fluid, each probe comprising:

a ring member;

a light source secured in the ring member;

light detection means secured in the ring member in a fixed position relative to the light source;

transmission means for transmitting light from the light detection means; and means for removably connecting the transmission means to the photodetector.

24. The apparatus of claim 23, wherein the transmission means allows the probe to move relative to the photodetector when the transmission means is connected to the photodetector.

25. The apparatus of claim 23, further comprising the photodetector and the computer.

26. The apparatus of claim 23, wherein at least one of the probes is submersible.

27. The apparatus of claim 23, wherein at least one of the probes has connectors to allow fluid conduits to be attached thereto.

28. The apparatus of claim 23, wherein at least one of the probes has a receptacle for holding sample fluid.

29. The apparatus of claim 23, wherein at least one of the probes has means for receiving a receptacle for holding sample fluid.

30. The apparatus of claim 23, wherein at least one of the probes has a handle.

31. A method of performing absolute macromolecular characterization with static light scattering, the method comprising:

submersing in a sample fluid a submersible probe for use with at least one photodetector and a computer electronically connected to the photodetector, the computer being programmed for analyzing data from static light scattering for performing absolute macromolecular characterization, the probe being submersible in a fluid to be sampled, the probe comprising:

a light source;

light detection means secured in a fixed position relative to the light source;

transmission means for transmitting light from the light detection means to the photodetector, the transmission means being of a sufficient length and flexibility to allow the submersible probe to be submersed in the fluid to be sampled without submersing the photodetector;

optically connecting the probe with a photodetector, the photodetector being electronically connected to a computer, the computer being programmed for analyzing data from static light scattering for performing absolute macromolecular characterization, the probe being submersible in a fluid to be sampled;

using the computer, analyzing data from static light scattering for performing absolute macromolecular characterization of the sample fluid in which the probe is submersed.

32. A method of performing absolute macromolecular characterization with static light scattering, the method comprising:

optically contacting a probe with a sample fluid containing a substance being studied, the probe having a scattering volume containing a small enough number of large scattering particles to not prevent absolute macromolecular characterization of the substance being studied;

optically connecting the probe to a photodetector, the photodetector being electronically connected to a computer with an interface, the computer being programmed for analyzing data from static light scattering for performing absolute macromolecular characterization;

using the computer, analyzing data from static light scattering for performing absolute macromolecular characterization of the sample fluid in optical contact with the probe, while electronically separating out scattering bursts from large scattering particles in the sample fluid, allowing hence the large scattering particles to also be counted and characterized, wherein:

the photodetector and the interface operate at a rate fast enough to electronically resolve the bursts.

33. The method of claim 32, wherein the rate is at least 2 Hz.

34. The method of claim 32, wherein the number of large scattering particles is less than 100 per scattering volume.

35. The method of claim 32, further comprising the step of counting and characterizing the large scattering particles.

36. A method of conducting absolute macromolecular characterization in real time in a polymerization reaction, comprising:

(a) diluting a sample fluid to be sampled to a concentration of such that interparticle effects do not dominate the scattering behavior;

(b) irradiating the diluted sample fluid with incident light;

(c) measuring light scattered from the diluted sample fluid with at least one photodetector and a computer electronically connected to the photodetector, the computer being programmed for analyzing data from static light scattering for performing absolute macromolecular characterization.

37. A method of conducting absolute macromolecular characterization in real time in a polymerization reaction, comprising:
(a) diluting a sample fluid to be sampled to a concentration of such that interparticle effects do not dominate the scattering behavior;
(b) irradiating the diluted sample fluid with incident light;
(c) measuring light scattered from the diluted sample fluid with at least one photodetector and a computer electronically connected to the photodetector, the computer being programmed for analyzing data from static light scattering for performing absolute macromolecular characterization,
wherein light is transmitted from the diluted sample fluid to the photodetector with a submersible probe comprising:
a light source for providing the incident light;
light detection means secured in a fixed position relative to the light source; and
transmission means for transmitting light from the light detection means to the photodetector, the transmission means being of a sufficient length and flexibility to allow the submersible probe to be submersed in the fluid to be sampled without submersing the photodetector.

38. A method of conducting absolute macromolecular characterization in real time in a polymerization reaction, comprising:
(a) diluting a sample fluid to be sampled to a concentration of such that interparticle effects do not dominate the scattering behavior;
(b) irradiating the diluted sample fluid with incident light;
(c) measuring light scattered from the diluted sample fluid with at least one photodetector and a computer electronically connected to the photodetector, the computer being programmed for analyzing data from static light scattering for performing absolute macromolecular characterization,
wherein the dimensionless quantity $2A_2cM_w$ is not greater than 10.

39. The method of claim 38, wherein the dimensionless quantity $2A_2cM_w$ is not greater than 2.

40. A method of conducting absolute macromolecular characterization in real time in a polymerization reaction, comprising:
(a) diluting a sample fluid to be sampled to a concentration of such that interparticle effects do not dominate the scattering behavior;
(b) irradiating the diluted sample fluid with incident light;
(c) measuring light scattered from the diluted sample fluid with at least one photodetector and a computer electronically connected to the photodetector, the computer being programmed for analyzing data from static light scattering for performing absolute macromolecular characterization,
wherein the photodetector has a scattering volume containing a small enough number of large scattering particles to not prevent absolute macromolecular characterization of the substance being studied;
using the computer, analyzing data from static light scattering for performing absolute macromolecular characterization of the sample fluid in optical contact with the probe, while electronically separating out scattering bursts from large scattering particles in the sample fluid, allowing hence the large scattering particles to also be counted and characterized, wherein:
the photodetector and the interface operate at a rate fast enough to electronically resolve the bursts.

41. Apparatus for static light scattering for absolute macromolecular characterization, comprising:
a probe for use with at least one photodetector and a computer electronically connected to the photodetector, the computer being programmed for analyzing data from static light scattering for performing absolute macromolecular characterization, the probe comprising:
a light source;
light detection means secured in a fixed position relative to the light source;
transmission means for transmitting light from the light detection means to the photodetector, the transmission means being of a sufficient length and flexibility to allow the probe to be used remote from the photodetector.

42. The apparatus of claim 41, wherein transmission means is 6 inches–100 feet long.

43. Apparatus for static light scattering, comprising:
an interchangeable probe for use with at least one light detector and a computer electronically connected to the photodetector, the computer being programmed for analyzing data from static light scattering for performing characterization of a fluid, the probe comprising:
a ring member;
a light source secured in the ring member;
light detection means secured in the ring member in a fixed position relative to the light source;
transmission means for transmitting light from the light detection means; and
means for removably connecting the transmission means to the photodetector.

44. The apparatus of claim 43, wherein the transmission means allows; the probe to move relative to the photodetector when the transmission means is connected to the photodetector.

45. The apparatus of claim 43, further comprising the photodetector and the computer.

46. The apparatus of claim 43, wherein the probe is submersible.

47. The apparatus of claim 43, wherein the probe has connectors to allow fluid conduits to be attached thereto.

48. The apparatus of claim 43, wherein the probe has a receptacle for holding sample fluid.

49. The apparatus of claim 43, wherein the probe has means for receiving a receptacle for holding sample fluid.

50. The apparatus of claim 43, wherein the probe has a handle.

51. The apparatus of claim 43, wherein the light detection means are placed at scattering angles of from about 10° to about 170°.

52. The apparatus of claim 43, wherein the ring member includes a beam dump.

53. The apparatus of claim 43, wherein the ring member is made of an opaque material.

54. The apparatus of claim 43, wherein the transmission means is of a sufficient length and flexibility to allow the probe to be used remote from the photodetector.

55. The apparatus of claim 43, further comprising means for using the apparatus for absolute macromolecular characterization.

56. The apparatus of claim 55, further comprising means for counting particles simultaneously.

57. The apparatus of claim 43, wherein the ring member contains a sampling cavity that can be directly contacted with sample fluid, which cavity can hold sample fluid which is introduced via flow, pipeting, immersion or other means, and which fluid can either remain stationary in the ring or flow through it.

58. The apparatus of claim 23, further comprising a plurality of photodetectors.

59. The method of claim 36, wherein the diluting of the sample fluid occurs on-line.

* * * * *